(12) United States Patent
Aylward

(10) Patent No.: US 6,787,161 B2
(45) Date of Patent: Sep. 7, 2004

(54) ANTI-CANCER COMPOUNDS

(75) Inventor: James Harrison Aylward, Queensland (AU)

(73) Assignee: Peplin Biotech Pty. Ltd., Fortitude Valley (AU)

(*) Notice: Subject to any disclaimer, the term of this patent is extended or adjusted under 35 U.S.C. 154(b) by 0 days.

(21) Appl. No.: 09/888,178

(22) Filed: Jun. 21, 2001

(65) Prior Publication Data

US 2002/0076457 A1 Jun. 20, 2002

Related U.S. Application Data

(63) Continuation of application No. 09/486,199, filed as application No. PCT/AU98/00656 on Aug. 19, 1998, now Pat. No. 6,432,452.

(30) Foreign Application Priority Data

Aug. 19, 1997 (AU) .............................................. PO8640

(51) Int. Cl.[7] ........................ A61K 35/78; A61K 31/12; A61K 31/045
(52) U.S. Cl. ................ 424/725; 424/195.18; 514/675; 514/691; 514/729; 514/738
(58) Field of Search .......................... 424/725, 195.18; 514/675, 491, 729, 738

(56) References Cited

U.S. PATENT DOCUMENTS

| | | | |
|---|---|---|---|
| 4,418,064 A | 11/1983 | Powell et al. | 424/248.54 |
| 4,560,774 A | 12/1985 | Pettit et al. | 549/267 |
| 4,716,179 A | * 12/1987 | Hecker et al. | |
| 5,145,842 A | 9/1992 | Driedger et al. | 514/63 |
| 5,643,948 A | 7/1997 | Driedger et al. | 514/533 |
| 5,716,968 A | 2/1998 | Driedger et al. | 514/323 |
| 5,750,568 A | 5/1998 | Driedger et al. | 514/533 |
| 5,886,017 A | 3/1999 | Driedger et al. | 514/410 |
| 5,886,019 A | 3/1999 | Driedger et al. | 514/410 |
| 5,891,870 A | 4/1999 | Driedger et al. | 514/183 |
| 5,891,906 A | 4/1999 | Driedger et al. | 514/450 |
| 5,932,613 A | * 8/1999 | Jiang et al. | |
| 6,432,452 B1 | * 8/2002 | Aylward | |

FOREIGN PATENT DOCUMENTS

| | | | |
|---|---|---|---|
| CN | 1077129 | 10/1993 | A61K/35/78 |
| CN | 1105246 | 7/1995 | A61K/35/78 |
| CN | 1112011 | 11/1995 | A61K/35/78 |
| CN | 1131037 | 9/1996 | A61K/35/78 |
| DE | 29 02 506 | 1/1979 | A61K/31/215 |
| EP | 0 330 094 | 8/1989 | A61K/35/78 |
| EP | 0 455 271 | 11/1991 | A61K/31/00 |
| EP | 0 310 622 | 4/1992 | A61K/31/00 |
| JP | 8-13571 | 1/1996 | E03C/1/20 |
| JP | 8-176002 | 7/1996 | A61K/35/78 |
| JP | 8-245505 | 9/1996 | A61K/31/215 |
| WO | WO 97/15575 | 5/1997 | C07D/487/02 |

OTHER PUBLICATIONS

El–Merzabani et al. Planta Med. 1979. vol. 36, pp. 150–155.*

M. Belkin et al.; *Tumor–Damaging Capacity of Plant materials. I. Plants Used as Cathartics*, Natl. Cancer Inst., 13, Apr. 7, 1952, pp. 139–149.

D. Weedon et al., *Home Treatment of Basal Cell Carcinoma*, Med. J. Aust., 1, Jun. 12, 1976, p. 928.

* cited by examiner

Primary Examiner—Christopher R. Tate
(74) Attorney, Agent, or Firm—Scully, Scott, Murphy & Presser

(57) ABSTRACT

This invention relates to a compound or group of compounds present in an active principle derived from plants of species *Euphorbia peplus*, *Euphorbia hirta* and *Euphorbia drummondii*, and to pharmaceutical compositions comprising these compounds. Extracts from these plants have been found to show selective cytotoxicity against several different cancer cell lines. The compounds are useful in effective treatment of cancers, particularly malignant melanomas and squamous cell carcinomas (SCCs). In a preferred embodiment of the invention, the compound is selected from the group consisting of jatrophanes, pepluanes, paralianes and ingenanes, and pharmaceutically-acceptable salts or esters thereof, and more particularly jatrophanes of Conformation II.

16 Claims, 13 Drawing Sheets

ANTI-CANCER COMPOUNDS

CROSS-REFERENCES TO RELATED APPLICATIONS

The present application is a continuation application of U.S. patent application Ser. No. 09/486,199, filed Jul. 28, 2000, now U.S. Pat. No. 6,432,452, which was filed under 35 U.S.C. §371 based on PCT/AU98/00656, filed on Aug. 19, 1998, which claims the benefit of priority to Australian Application No. PO-8640, filed Aug. 19, 1997. These applications are explicitly incorporated herein by reference in their entirety and for all purposes.

This invention relates to a compound or group of compounds present in an active principle derived from the family Euphorbiaceae, and in particular in plants of the species *Euphorbia peplus, Euphorbia hirta* and *Euphorbia drummondii*. Extracts from these plants have been found to show selective cytotoxicity against several different cancer cell lines. Compounds present in the sap of Euphorbia spp. are useful in effective treatment of cancers, particularly malignant melanomas and squamous cell carcinomas (SCCs).

BACKGROUND OF THE INVENTION

There is a strong association between exposure of the skin to the ultraviolet light component of sunlight and the development of skin cancers, such as malignant melanoma and the non-melanoma skin cancers, mainly basal cell carcinomas (BCCs) and squamous cell carcinomas (SCCs). The incidence of these cancers has been rapidly increasing world wide. In Britain, there were 4000 newly-diagnosed cases of malignant melanoma in 1994, an 80% increase over the past 10 years (Wessex Cancer Trust, 1996). In the United States, approximately 34,100 new cases were expected, an increase of 4% per year. Queensland, Australia, has the highest incidence of melanoma in the world, but early detection and widespread public health campaigns and the promotion of the use of sunscreens and reduction of ultraviolet exposure have helped to reduce the number of deaths. BCCs currently affect one in 1,000 in the U.K. population, and the incidence has more than doubled in the last 20 years (Imperial Cancer Research Fund, U.K., 1997). One million new cases of BCCs and SCCs are expected to be diagnosed in the USA in 1997, compared to 600,000 in 1990 and 400,000 in 1980 (National Oceanic and Atmospheric Administration U.S.A., 1997). In Australia, there is no reason to suspect that a similarly increasing incidence would not also apply, despite extensive publicising of the dangers or solar and UV radiation, with the Queensland population being at the greatest risk.

Over 90% of all skin cancers occur on areas of the skin that have been regularly exposed to sunlight or other ultraviolet radiation, with U.V.B. responsible for burning the skin and associated with malignant melanomas, and U.V.A. associated with premature skin aging and the development of BCCs and SCCs (Wessex Cancer Trust, 1996). Childhood sun exposure has been linked to the development of malignant melanoma in younger adults. Other risk factors include a genetic predisposition (fair complexion, many skin moles), chemical pollution, over-exposure to X-rays, and exposure to some drugs and pesticides. Depletion of the ozone layer of the stratosphere is considered to contribute to long-term increases in skin cancer.

Surgical removal is by far the most common treatment for malignant melanomas, BCCs and SCCs. This can take the form of electrodesiccation and curettage, cryosurgery, simple wide excision, micrographic surgery or laser therapy. Other treatments, used when the cancers are detected at a later stage of development, are external radiation therapy, chemotherapy or to a lesser extent bio-immunotherapy or photodynamic therapy. The choice of treatment is dependent on the type and stage of the disease and the age and health of the patient (National Cancer Institute, U.S.A., 1997).

All of the present treatments suffer from severe limitations. The major concern is the poor recognition of cancerous cells at the site of excision and the high likelihood of recurrence, necessitating follow-up surgery and treatment, with the risk of further disfigurement and scarring. In one publication, the reported rates for incompletely-excised BCCs was 30–67% (Sussman and Liggins, 1996). Immune suppression associated with surgery may cause any remaining cells to proliferate, and increase the risk of metastases. In melanoma patients there is a high risk that the cancer has already metastasized at the time of initial surgery, and late recurrence leading to death is common. Present alternatives to surgery, such as radiation therapy and chemotherapy, also carry risks of immune suppression and poor specificity. Immunotherapy and gene therapy hold the greatest promise, but the rational application of these is likely to be still decades away.

When the tumour is past the stage amenable to surgery, the most common treatment for melanoma or metastatic skin cancer of all types is chemotherapy, which has been largely unsuccessful (Beljanski and Crochet, 1996).

In theory, an ideal drug would be one that when applied topically to an exposed melanoma, BCC or SCC, selectively necrotises the tumour cells or induces them to undergo apoptosis, without causing damage to the surrounding healthy skin cells. In practice, this has yet to be achieved. The drugs currently available are neither selective nor penetrative.

The lay public is also enamoured of the concept of topical chemotherapy. There have been many documented "home remedies" for skin cancer, which have had disastrous consequences, e.g. the use of boot polish (Adele Green, Queensland Institute of Medical Research, pers. Comm.). The major danger is the production of scar tissue, underneath which the tumour cells continue to grow. An extract derived from plants of the genus Solanum (kangaroo apple or devil's apple) and purportedly containing solasodine glycosides has been available in Australia as a non-prescription preparation treatment of sunspots and solar keratoses, under the name "Curaderm". However the preparation was shown in a small clinical trial against BCCs to be ineffective, with 14/20 patients showing persisting tumour on histological examination of tissue from the treated site. In some cases, histological examination of the site of treatment revealed malignant tissue embedded in scar tissue. The authors warned against self-diagnosis and treatment, particularly with irritant substances (Francis et al, 1989).

However, anecdotal reports suggest that plant sap extracts are still being used by the general public for the treatment of sunspots or solar keratoses, with some success being claimed.

The sap of plants of the family Euphorbiaceae, particularly the genus Euphorbia, has been used in the folk medicine of many countries. The genus was named after an early Greek physician in deference to its purported medicinal properties (Pearn, 1987). Only recently have some of these claims been investigated scientifically. The genus is enormously diverse, ranging from small, low-growing herbaceous plants to shrubs and trees. Nearly all reports of activity of these plants and their extracts are anecdotal or derived from traditional medicine, and the nature of the preparations used is frequently either unknown or very poorly described. Activity has been claimed against a huge variety of conditions, ranging from warts, "excrescences", calluses, "cheloid tumours", corns, whitlows or felons, "superfluous flesh" and the like, to a variety of cancers (see, for example, Hartwell: Lloydia 1969 32 153).

As part of the screening program for anti-cancer activity carried out on 114,000 extracts from 35,000 terrestrial plant species carried out by the United States National Cancer Institute, a number of species of Euphorbia were tested. An aqueous suspension, an olive-oil suspension, an alcohol extract and an acid extract were screened for activity against the transplantable tumour cell line sarcoma 37. Four species were tested. Of these, *Euphorbia peplus* showed no activity in any of the extracts; *Euphorbia drummondii, Euphorbia pilulifera*, and *Euphorbia resinifera* showed weak activity of an acid extract, an alcohol extract, and an olive-oil suspension respectively (Belkin and Fitzgerald, 1953). A review of the scientific and medical literature of the past five years revealed a diversity of powerful active principles such as di- and tetra-terpenes, flavonoids, sterols and proteins in this genus, and many bioactive effects have been reported, with both positive and adverse effects noted. These reports are summarized in Table 1. In particular the genus Euphorbia is well known to produce tumour promoters such as phorbol esters (Hecker, E.: "Cocarcinogens from Euphorbiaceae and Thymeleaceae" in "Symposium on Pharmacognosy and Phytochemistry" (Wagner et al, eds., Springer Verlag 1970 147–165)).

TABLE 1

| Species | Active principle | Action | Reference |
|---|---|---|---|
| Euphorbia aleppica | whole plant: aleppicatines, diterpene polyesters, cycloartene triterpenes, scopoletin, kaempferol, 4-hydroxybenzoic acid | prostatic and lung neoplasms | Oksuz, S. et al (1996) |
| Euphorbia biglandulosa Desf. | cerebrosides | ? | Falsone G et al |
| Euphorbia bougheii | latex | skin irritant and tumor promoting effect | Gundidza, M. et al (1993) |
| Euphorbia characias | latex: lipase | homology (43.5%) with B chain of ricin | Moulin, A. et al (1994) |
| Euphorbia cooperei NE Br | whole plant: phorbol ester | skin irritant | Gundidza, M. et al (1992) |
| Euphorbia fisheriana | alkaline extract | treatment of epilepsy | Liu Y. et al (1994) |
| Euphorbia hirta | whole plant | inhibition of bacteria of Shigella spp | Vijaya, K. et al (1995) |
| Euphorbia hirta | whole plant: flavonoid | antidiarrhoeic activity | Galvez, J. et al (1993) |
| Euphorbia humifusa | whole plant: hydrolysable tannins, polyphenol glucoside | ? | Yashida, T. et al (1994) |
| Euphorbia hylonoma | root: 3,3',4-tri-O-metmethylellagic acid, beta-sitosterol | Chinese herbal medicine?? action | Guo, Z. et al (1995) |

TABLE 1-continued

| Species | Active principle | Action | Reference |
|---|---|---|---|
| Euphorbia kansui | whole plant: ingenols | stimulation of expression of the macrophage Fc receptor | Matsumoto, T. et al (1992) |
| Euphorbia lathyris | pelletised plant material | rodenticide | Gassling and Landis (1990) U.S. Pat. No. 4906472 |
| Euphorbia marginata | latex | mitogenic lectin | Stirpe, F. et al (1993) |
| Euphorbia peplus | ? quercetin, hyperoside, kaempferol, sitosterol, alkaloids, glycosides | Folk remedies for warts, corns, asthma, rodent ulcer, BCC | Weedon and Chick (1976) and references cited therein |
| Euphorbia poisonii | diterpenes | selectively cytotoxic for human kidney carcinoma cell line A-498 | Fatope, M.O. et al (1996) |
| Euphorbia splendens | latex | inhibition of mollusc Biomphalaria glabrata (Vectors of schistosomiasis) | Jurberg, P. et al (1995) |
| Euphorbia tirucalli | whole plant | reduces EBV-specific cellular immunity in Burkitt's lymphoma | Imai, S. (1994) |

The most intensively studied species of this group is *Euphorbia pilulifera* L (synonyms *E. hirta* L.; *E. capitata* Lam.), whose common names include pill-bearing spurge, snake-weed, cat's hair, Queensland asthma weed and flowery-headed spurge. The plant is widely distributed in tropical countries, including India, and in Northern Australia, including Queensland. According to the "Encyclopedia of Common Natural Ingredients Used in Food, Drugs and Cosmetics" (Leung and Foster, 1996), the whole flowering or fruiting plant is used in herbal remedies, principally for cough preparations, and in traditional medicine for treatment of respiratory conditions such as asthma, bronchitis, coughs and hayfever. This reference reports the active constituents of *Euphorbia pilulifera* to be choline and shikimic acid, and that other compounds present include triterpenes, sterols, flavonoids, n-alkanes, phenolic acids, L-inositol, sugars and resins. Of these components, shikimic acid is an essential intermediate in the synthesis of aromatic amino acids, and has been reported to have carcinogenic activity in mice (Evans and Osman, 1974; Stavric and Stoltz, 1976). Jatrophanes, ingenanes, and a tetracyclic diterpene designated pepluane were identified in the sap of *Euphorbia peplus* by Jakupovic et al (1998a). The jatrophanes were stated to have a different conformation from those of previously-known jatrophanes. Jatrophanes are also stated to belong to a group of non-irritant diterpenes, which could have accounted to their being overlooked in previous studies. There is no disclosure or suggestion at all of any biological activity of the jatrophanes or of the new pepluane compound; nor is it suggested that any of these compounds might be useful for any pharmaceutical purpose.

A recent report describes selective cytotoxicity of a number of tigliane diterpene esters from the latex of *Euphorbia poisonii*, a highly-toxic plant found in Northern Nigeria, which is used as a garden pesticide and reputed to be used in homicides. One of these compounds has a selective cytotoxicity for the human kidney carcinoma cell line A-498 more than 10,000 times greater than that of adriamycin (Fatope et al, 1996).

In a series of patent applications, Tamas has claimed use of *Euphorbia hirta* plants and extracts thereof for a variety of purposes, including tumour therapy (EP 330094), AIDS-related complex and AIDS (HU-208790) and increasing immunity and as an antifungoid agent for treatment of open wounds (DE-4102054).

Thus, while there are isolated reports of anti-cancer activity of various Euphorbia preparations (see Fatope et al, 1996; Oksuz et al, 1996), not only are the compounds present in at least one Euphorbia species reported to be carcinogenic (Evans and Osman, 1974; Stavric and Stolz, 1976; Hecker, 1970; 1977), but at least one species has a skin-irritant and tumour-promoting effect (Gundidza et al, 1993), and another species reduces EBV-specific cellular immunity in Burkitt's lymphoma (Imai, 1994).

To our knowledge, there has been no reliable or reproducible report of the use of any extract from Euphorbia species for the treatment of malignant melanoma or SCCs. An anecdotal report of home treatment of a BCC with the latex of *Euphorbia peplus* (petty spurge or milk weed) was the publication of Weedon, D. and Chick, J., entitled "Home treatment of basal cell carcinoma" (1976). The authors stated that medicinal propeties have been claimed for the milky juice of this plant since the time of Galen, and it was widely used as a home remedy for corns, warts, and asthma. At the turn of the century it was used by some physicians in Sydney for the treatment of rodent ulcers. The author's patient claimed to have treated himself over many years for multiple BCCs.

"The patient, a 54 year old male, had been seen sporadically at the Royal Brisbane Hospital since 1971. On one visit he was noted to have a clinical basal cell carcinoma on the anterior part of his chest which was confirmed by biopsy of a tiny specimen taken from one edge. Some days later when the biopsy site had healed the patient applied the sap of *Euphorbia peplus* every day for 5 days. The area became erythematous and then pustular, after which the lesion sloughed off. On his return 6 weeks after treatment, the patient agreed to let us surgically excise the small area of residual scarring. Multiple sections showed dermal scar tissue which contained a few chronic inflammatory cells, but showed no evidence of residual tumour."

The authors stated that "this communication should in no way be taken as a recommendation of the form of therapy". There are a few reports cautioning on the corrosive nature of the sap, and minor eye damage that has resulted from the home treatment of warts using *Euphorbia peplus* (Eke, T., 1994). It appears likely that the effect reported by Weedon and Chick resulted from the irritant activity of the *Euphorbia peplus* sap, and that, as in the case of the Solanum extract "Curaderm" reported by Francis et al (1989), there is a high risk of residual tumour cells surviving in or under the scar tissue that results from such treatment.

The inventor has now surprisingly found that sap of plants from three different Euphorbia species, *Euphorbia peplus*, *Euphorbia hirta* and *Euphorbia drummondii*, specifically inhibits growth of three different human tumour cell lines, including malignant melanoma. Moreover, at very low concentrations, sap from *Euphorbia peplus* and *Euphorbia hirta* induced differentiation of malignant melanoma cells so that they adopted the morphological appearance of normal melanocytes. At similar or even lower concentrations an extract stimulated activation of the metallothionein gene promoter and expression of a reporter gene in MM96L malignant melanoma cells. The results were particularly striking, since the melanoma cell line which was used is refractory to inhibition by all of the conventional chemotherapeutic agents which have been tested against it (Maynard and Parsons, 1986).

SUMMARY OF THE INVENTION

In a first aspect, the invention provides a compound or compounds present in plants of the genus Euphorbia, and in particular in sap of *Euphorbia peplus*, *Euphorbia hirta* and/or *Euphorbia drummondii*, which:

(a) is able to kill or inhibit the growth of cancer cells, but does not significantly affect normal neonatal fibroblasts, or spontaneously transformed keratinocytes;

(b) has activity which is not destroyed by heating at 95% for 15 minutes;

(c) has activity which is not destroyed by treatment with acetone;

(d) has activity which can be extracted with 95% ethanol; and (e) stimulates metallothionein gene activation.

Preferably, the compound(s) is able to inhibit the growth of at least one cell line selected from the group consisting of MM96L, MM229, MM220, MM237, MM2058, B16, LIM1215, HeLa, A549, MCF7, MCC16 and Colo16 as herein defined. More preferably, the compound(s) is able to inhibit growth of or to induce differentiation in MM96L cells.

Even more preferably the compound is also able to induce normal melanocytes to proliferate.

Preferably, the compound is present in sap of *E. peplus* or *E. hirta*.

It will be clearly understood that while the invention is described in detail with reference to compounds detected in sap or sap extracts, these compounds, when present in or extracted from whole plants or parts thereof, are still within the scope of the invention.

In a second aspect, the invention provides a composition comprising an active compound as described above, together with a pharmaceutically-suitable carrier or diluent.

More preferably the compound is selected from the group consisting of jatrophanes, pepluanes, paralianes and ingenanes.

Where the compound is a jatrophane, it is preferably of Conformation II as defined by Jakupovic et al (1998a). It will be clearly understood that the substitutions observed in naturally-occurring jatrophane, pepluane and paraliane skeletons are within the scope of the invention. These include the following substitutions and analogues.

Compounds of this type have been found in a variety of plants of the genus Euphobia (Jakupovic et al, 1998a, b, c; Marco et al, 1998).

TABLE 2

Natural Substitutions Observed for the Jatrophane, Pepluane and Paraliane Skeletons. (Jakupovic et al, 1998 a, b, c; Marco et al, 1998)

| Carbon position | Jatrophane | Pepluane | Paraliane |
|---|---|---|---|
| 1 | H, OAc | $H_2$, OAc | H & OAc, $H_2$ |
| 2 | OAc & H, $CH_3$ & OAc, $CH_3$ & H | $CH_3$ & H | $CH_3$ & H, $CH_3$ & OAc |

TABLE 2-continued

Natural Substitutions Observed for the Jatrophane, Pepluane and Paraliane Skeletons. (Jakupovic et al, 1998 a, b, c; Marco et al, 1998)

| Carbon position | Jatrophane | Pepluane | Paraliane |
|---|---|---|---|
| 3 | OH, OAc, OiBu, OCinn, OBz, OBzOCH$_2$CO, PhCO$_2$CH$_2$CO$_2$ | OBz | OBz |
| 4 | H | H | H |
| 5 | OAc, OiBu, Omebu, OAcOAc | OAc | OAc |
| 6 | exocyclic double bond | CH$_3$, CH$_2$OAc | CH$_3$, CH$_2$OAc |
| 7 | H$_2$, OAc, OiBu, OMeBu, OPr, OCOiPr, OCOEt | H$_2$, | H$_2$, |
| 8 | H$_2$, OH, OAc, OiBu OMebu, OBz, OAng, | OAc, double bond to C12 | H, OAc |
| 9 | OH, OAc, OCinn, ONic, =O | OAc, 9–18 double bond | =O |
| 10 | (CH3)$_2$ | CH$_3$ & OAc, double bond to 11, CH$_3$ | (CH3)$_2$ |
| 11 | double bond to 12 | H$_2$, double bond to 10 & OH | H$_2$ |
| 12 | double bond to 11 | H, double bond to 8 | H |
| 13 | CH$_3$ | CH$_3$ | CH$_3$ |
| 14 | H & OH, H & OAc, =O | OAc | OAc |
| 15 | OAc, OH | OH | OH |
| 18 | | H, H$_2$, | |

Ac=CH$_3$CO, Me=CH$_3$, Et=CH$_3$CH$_2$, iBu=(CH$_3$)$_2$CHCO, Ph=C$_6$H$_5$, Cinn=PhCHCHCO, OBz=C$_6$H$_5$COO, OMebu=OCH$_3$CH$_2$CH(CH$_3$)CO, ONic=C$_5$H$_4$NCO$_2$,, Pr=CH$_3$CH$_2$CH$_2$, iPr=CH(CH$_3$)$_2$, Ang=CH$_3$CHC(CH$_3$)CO Even more preferably, the compound is selected from the group consisting of:

5,8,9,10,14-pentaacetoxy-3-benzoyloxy-15-hydroxypepluane (pepluane);

15-pentaacetoxy-9-nicotinoyloxy-14-oxojatropha-6(1),11E-diene (jatrophane 1);

2,5,7,9,14-hexaacetoxy-3-benzoyloxy-15-hydroxy-jatropha-6(17),11E-diene (jatrophane 2);

2,5,14-triacetoxy-3-benzoyloxy-8,15-dihydroxy-7-isobutyroyloxy-9-nicotinoyloxyjatropha-6(17),11E-diene (jatrophane 3);

2,5,9,14-tetraacetoxy-3-benzoyloxy-8,15-dihydroxy-7-isobutyroyloxyjatropha-6(17),11E-diene) (jatrophane 4);

2,5,7,14-tetraacetoxy-3-benzoyloxy-8,15-dihydroxy-9-nicotinoyloxyjatropha-6(17),11E-diene (jatrophane 5);

2,5,7,9,14-pentaacetoxy-3-benzoyloxy-8,15-dihydroxyjatropha-6(17),11E-diene (jatrophane 6);

20-acetyl-ingenol-3-angelate;

and pharmaceutically-acceptable salts or esters thereof.

In one preferred embodiment of the invention, the composition additionally comprises β-alanine betaine hydrochloride or t-4-hydroxy-N,N-dimethyl proline.

In a third aspect, the invention provides a method of treatment of a cancer, comprising the step of administering an anti-cancer effective amount of a compound of the invention to a mammal in need of such treatment.

Preferably, the cancer is a solid tumour. More preferably, the cancer is selected from the group consisting of malignant melanoma, other skin cancers including Merkel cell carcinoma, squamous cell carcinoma and basal cell carcinoma, lung cancer, colon cancer, prostate cancer, cervical cancer and breast cancer.

In a fourth aspect, the invention provides a method of inhibiting proliferative activity of neoplastic cells, comprising the step of exposing the cells to an anti-proliferative amount of a compound of the invention. The cells may be treated either ex vivo or in vivo.

In a fifth aspect, the invention provides a method of preventing or alleviating damage to skin, caused by ultraviolet irradiation, ionizing radiation, microwave radiation, exposure to ozone, or the like, comprising the step of topically administering an effective amount of a compound of the invention to a subject in need of such treatment. This aspect of the invention may be used in the treatment of solar keratosis, skin damage occurring during radiotherapy, and the like.

In a sixth aspect the invention provides a method of stimulating proliferation of non-neoplastic cells comprising the step of exposing the cells to a proliferation-inducing amount of a compound or a composition of the invention. This is useful in inducing regeneration of tissues and, because T-lymphocytes proliferate in response to the compositions of the invention, is useful in promoting the immune response to disease states.

The mammal may be a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, cattle and sheep, or zoo animals such as felids, canids, bovids, and ungulates.

The compounds and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case. It is contemplated that compounds of the invention may be administered orally, topically, and/or by parenteral injection, including intravenous injection.

Methods and pharmaceutical carriers for preparation of pharmaceutical compositions are well known in the art, as set out in textbooks such as Remington's Pharmaceutical Sciences, 17th Edition, Mack Publishing Company, Easton, Pa., USA.

For the purposes of this specification it will be clearly understood that the word "comprising" means "including but not limited to", and that the word "comprises" has a corresponding meaning.

A: Spots 34–45 were visualised on a UV light box. Activities were scored towards MM96L at a 1 in 500 dilution (+++=no effect, −=complete cell death, d=100% reversion of cells to a dendritic appearance.

B: Spots 14–20 were visualised on a UV light box. Activities were scored towards MM96L at a 1 in 500 dilution (+++=no effect, −=complete cell death, d=100% reversion of cells to a dendritic appearance.

C: Spots 21–27 were visualised on a UV light box. Activities were scored towards MM96L at a 1 in 500 dilution (+++=no effect, −=complete cell death, d=100% reversion of cells to a dendritic appearance.

Figure 9:
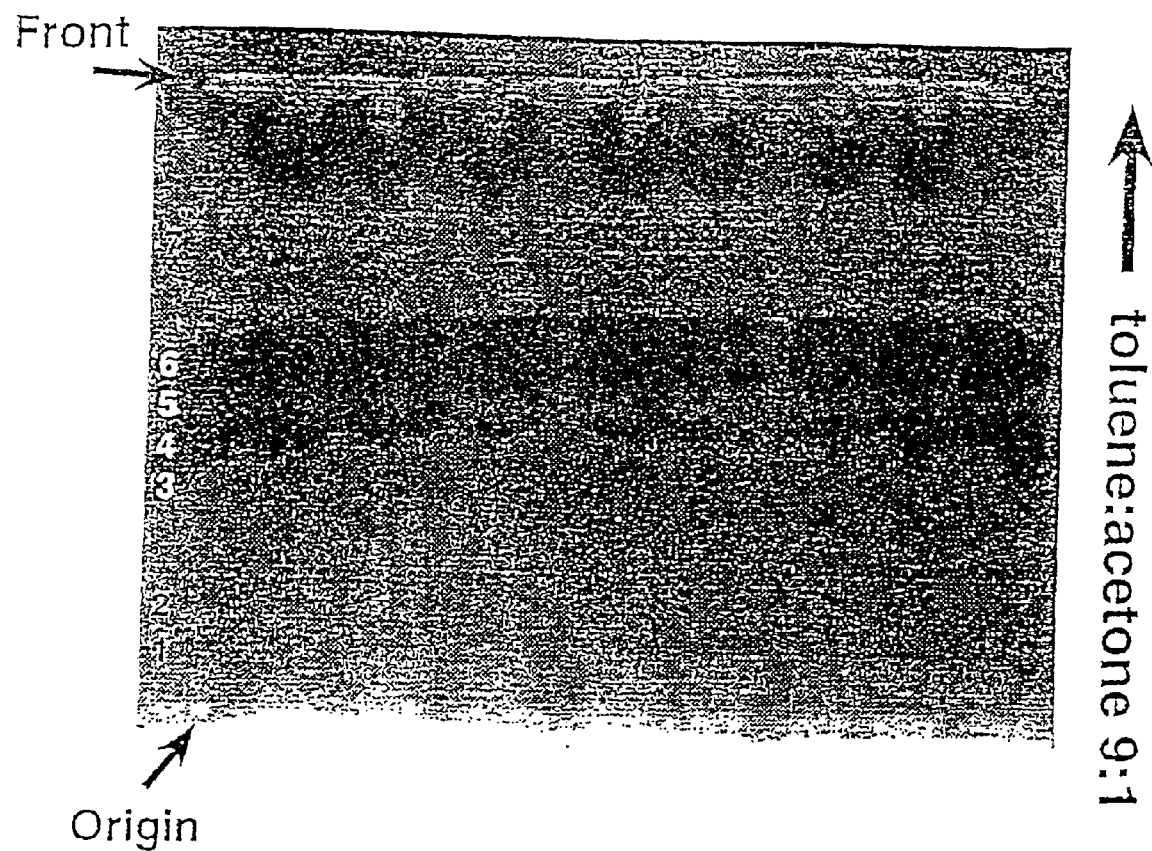
Figure 10:
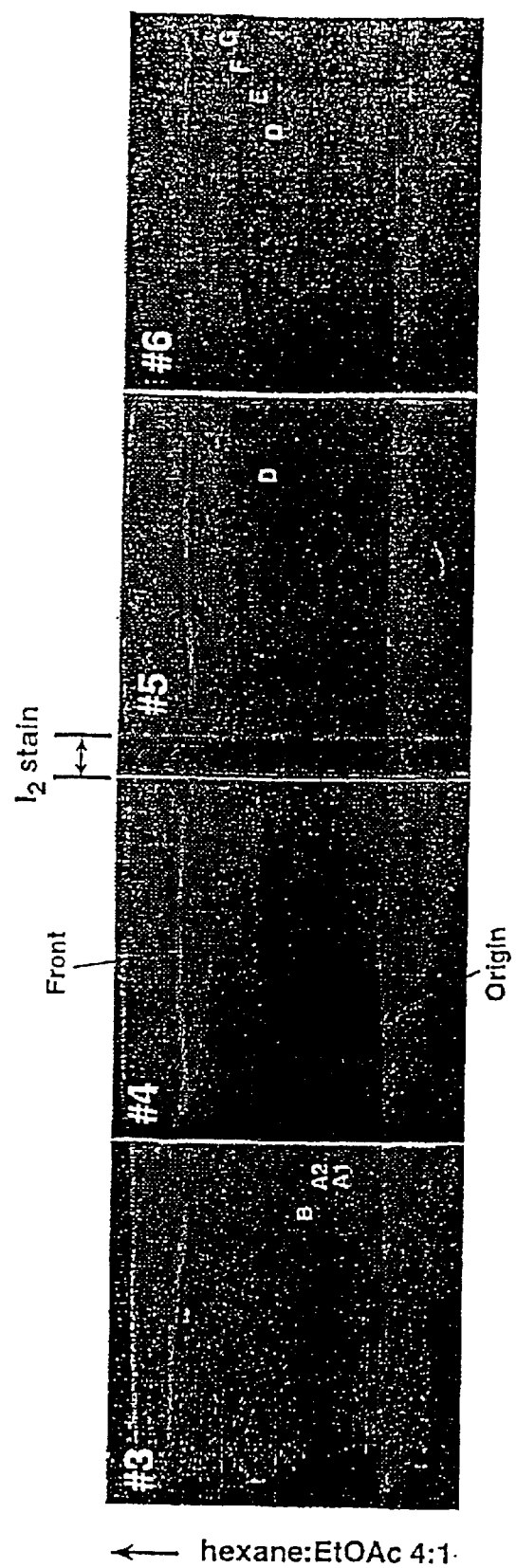

FIG. 9 shows results of ascending chromatography of crude sap on HPTLC using a toluene:acetone (9:1) solvent system. Opaque bands 1–7 were visualised on a UV light box FIG. 10 shows results of ascending chromatography of fraction 1 from FIG. 9 on HPTLC using a hexane:ethyl acetate (4:1) solvent system. Bands A–G were visualised on a UV light box. (Side strip stained with 0.1% iodine in chloroform revealed Fraction G—inactive against MM96L).

Figure 11:
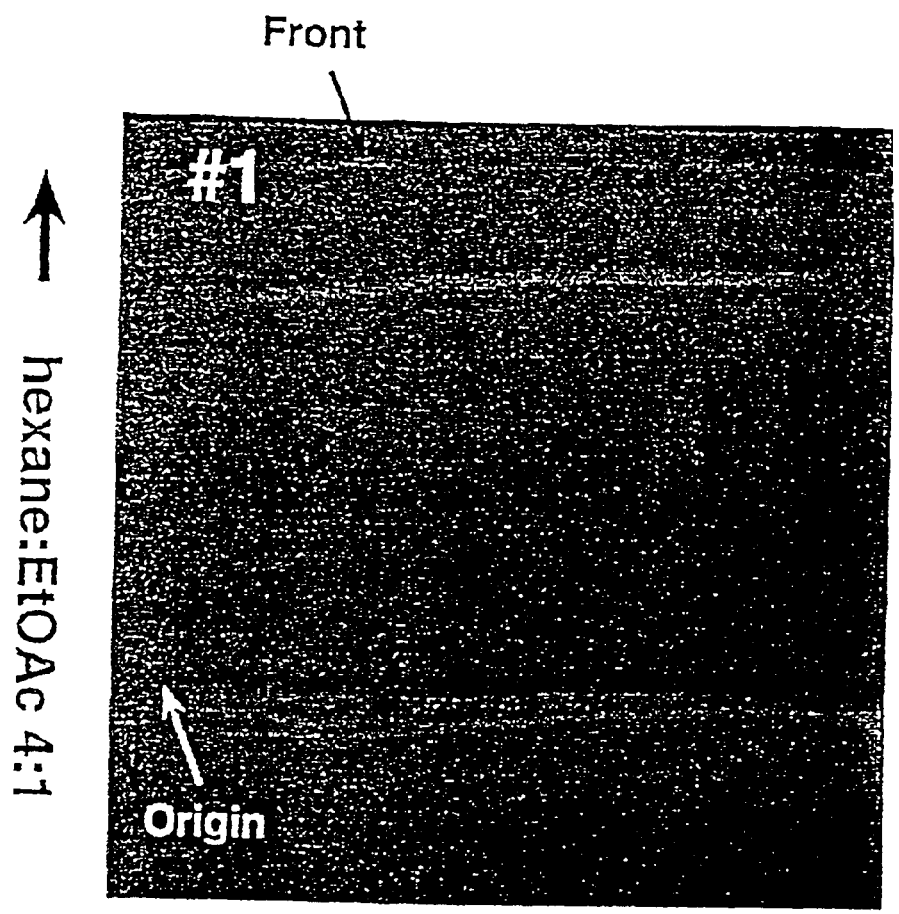

FIG. 11 shows results of ascending chromatography of fraction 1 from FIG. 9 on HPTLC using a hexane:ethyl acetate (4:1) solvent system. Band H was visualised on a UV light box.

Figure 12:
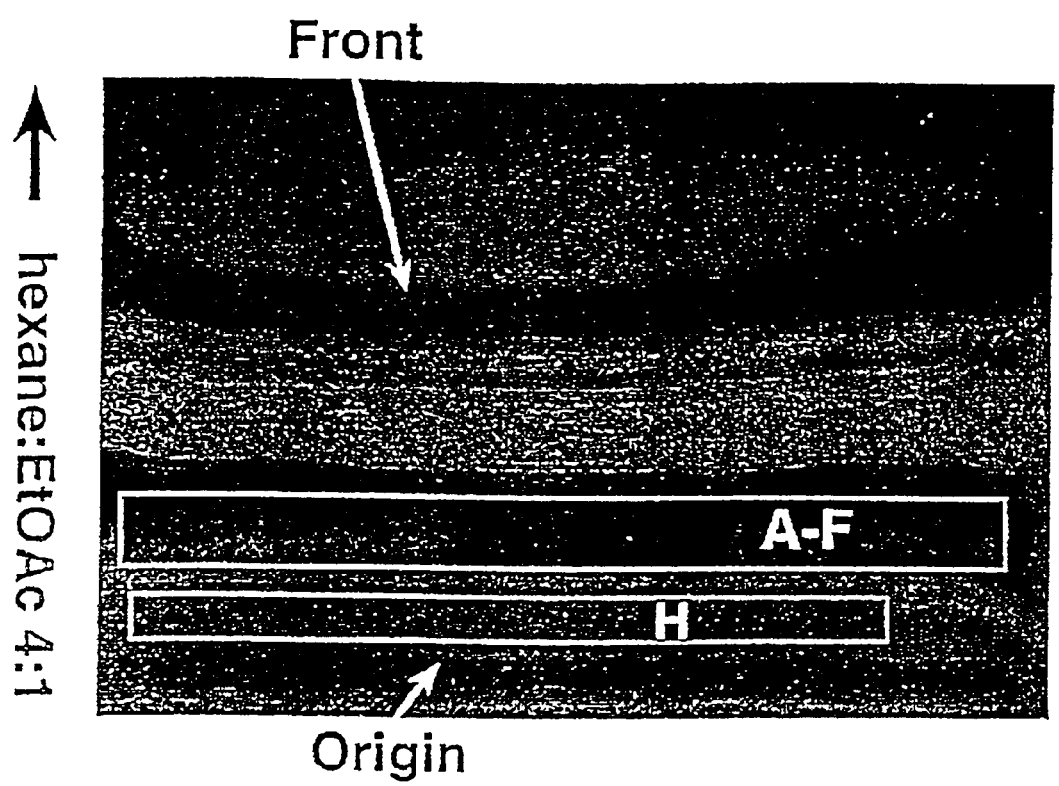

FIG. 12 shows the results of ascending chromatography of diethyl ether soluble fraction prepared from crude sap on preparative thin layer chromatography (PLC, Merck) using hexane:ethyl acetate (4:1) solvent system. Zones H and A–F were visualised on a UV light box, extracted, and used for in vivo studies.

Figure 13:
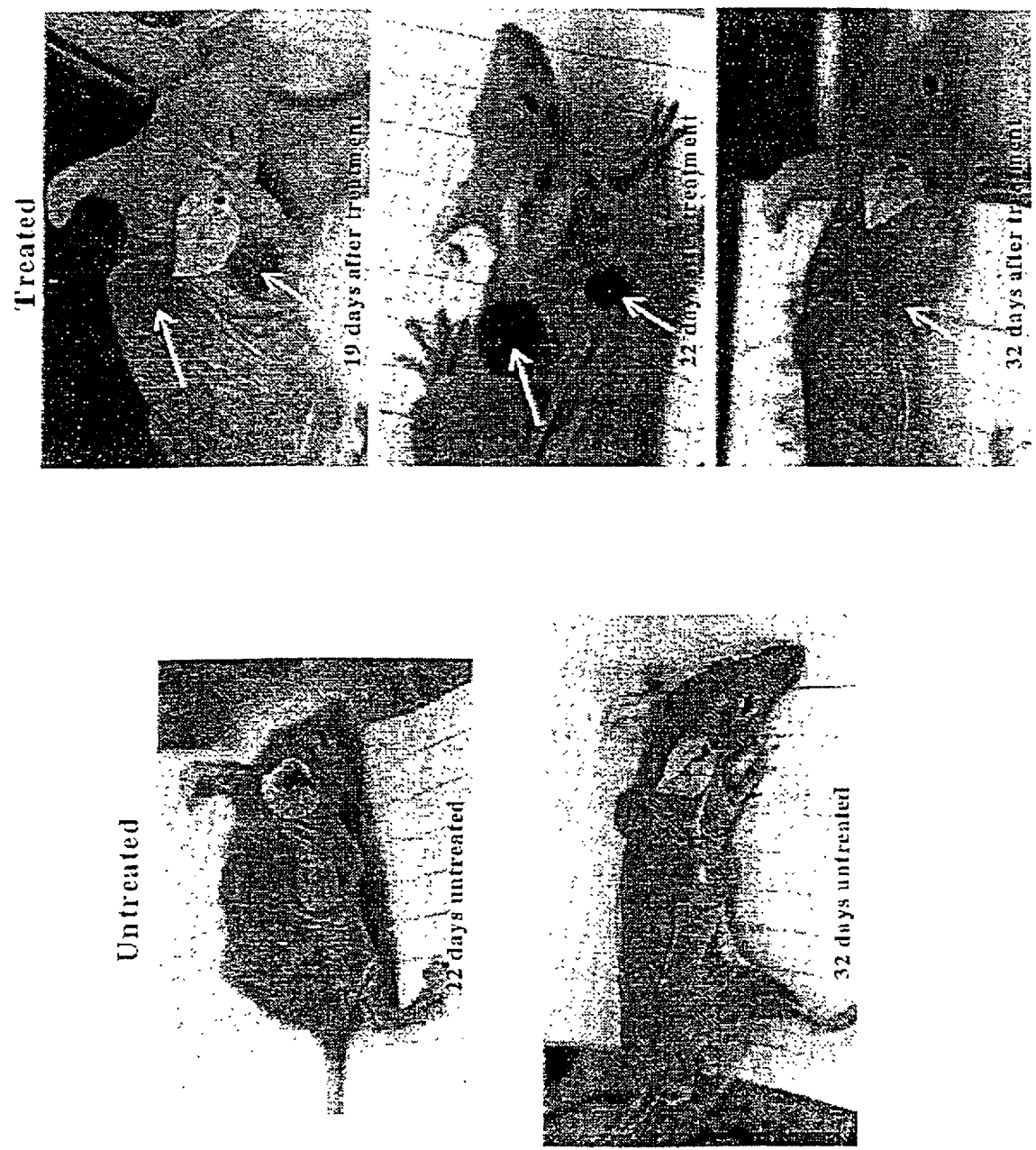

FIG. 13 shows the results of treatment of subcutaneous human melanoma MM96L xenografts in nude mice with a partially purified fraction prepared as described in Example 11. Arrows denote the position of topical treatments for a tumour (right-hand side) and for normal skin (top of back). There was no evidence of residual tumour growth or lasting damage to the normal skin 32 days after the treatment regimen began, and 20 days after the first topical application.

DETAILED DESCRIPTION OF THE INVENTION

The invention will be described in detail by reference only to the following non-limiting examples and to the figures.

EXAMPLE 1

Inhibitory Activity of Euphorbia Sap Against Tumour Cell Lines

The ability of sap of three Euphorbia species, *Euphorbia peplus*, *Euphorbia hirta* and *Euphorbia drummondii* to inhibit the growth of three different human tumour cell lines was tested. The activity against normal skin fibroblasts was tested as a control.

The cell lines were maintained in RPMI medium containing 5% foetal calf serum (FCS), and assays were performed in the same medium.

Sap was collected from plants growing randomly on cultivated soil on a farm at Palmwoods, in the Sunshine Coast hinterland, South-East Queensland. The plant stem surface was briefly washed with 70% ethanol, and scissors washed in ethanol were used to cut the stem and release the milky latex sap. The sap was collected into 10 ml sterile plastic centrifuge tubes, transported at 4° C. to Brisbane and stored frozen at −20° C. Prior to use, the sap was serially diluted five-fold up to 1 in 3125 into sterile 1.5 ml Eppendorf tubes using sterile MilliQ water. 10 μL aliquots of each dilution were added to each two of microtitre plate wells containing 100 μl of the cell lines. Assays were performed in duplicate.

After 5 days, cells were examined blind, for inhibition of growth compared to control untreated cell samples. The results are summarized in Tables 3 to 6, in which the cell lines tested were

| | |
|---|---|
| NFF | normal skin fibroblasts |
| MM96L | malignant melanoma, brain metastasis |
| HeLa | cervical cancer |
| HACat | spontaneously- transformed human keratinocytes | and the scale is 0=no effect to 5=complete cell death.

The dilution in the table heading refers to the dilution of the sample before addition to the culture. Thus, the dilution in the final culture is approximately 10-fold greater.

TABLE 3

NFF Normal Fibroblasts

| | Dilution | | | | | | | | | |
|---|---|---|---|---|---|---|---|---|---|---|
| | Sample 1 | | | | | Sample 2 | | | | |
| Sample | 1/5 | 1/25 | 1/125 | 1/625 | 1/3125 | 1/5 | 1/25 | 1/125 | 1/625 | 1/3125 |
| E. peplus | 3 | 2 | 0 | 0 | 0 | 0 | 0 | 0 | 0 | 0 |
| E. hirta | 5 | 0 | 0 | 0 | 0 | 0 | 0 | 0 | 0 | 0 |
| E. drummondii | 4 | 0 | 0 | 0 | 0 | 0 | 0 | 0 | 0 | 0 |
| No addition | 0 | 0 | 0 | 0 | 0 | 0 | 0 | 0 | 0 | 0 |

TABLE 4

MM96L Malignant Melanoma

| | Sample 1 | | | | | Sample 2 | | | | |
|---|---|---|---|---|---|---|---|---|---|---|
| | Dilution | | | | | | | | | |
| Sample | 1/5 | 1/25 | 1/125 | 1/625 | 1/3125 | 1/5 | 1/25 | 1/125 | 1/625 | 1/3125 |
| E. peplus | 5 | 4 | 4 | 0 | 0 | 5 | 3 | 1 | 0 | 0 |
| E. hirta | 5 | 4 | 1 | 0 | 0 | 4 | 1 | 0 | 0 | 0 |
| E. drummondii | 5 | 2 | 1 | 0 | 0 | 5 | 2 | 0 | 0 | 0 |
| No addition | 0 | 0 | 0 | 0 | 0 | 0 | 0 | 0 | 0 | 0 |

TABLE 5

Hela Cells

| | Dilution | | | | |
|---|---|---|---|---|---|
| Sample | 1/5 | 1/25 | 1/125 | 1/625 | 1/3125 |
| E. peplus | 5 | 3.5 | 3 | 1 | 1 |
| E. hirta | 5 | 5 | 5 | 5 | 0 |
| E. drummondii | 5 | 0 | 0 | 0 | 0 |
| No addition | 0 | 0 | 0 | 0 | 0 |

TABLE 6

HACat keratinocytes

| | Dilution | | | | |
|---|---|---|---|---|---|
| Sample | 1/5 | 1/25 | 1/125 | 1/625 | 1/3125 |
| E. peplus | 4 | 0 | 0 | 0 | 0 |
| E. hirta | 5 | 0 | 0 | 0 | 0 |
| E. drummondii | 5 | 0 | 0 | 0 | 0 |
| No addition | 0 | 0 | 0 | 0 | 0 |

From these results it can be seen that:
a) E. peplus was active against HeLa cells, and to a lesser extent against MM96L cells.
b) E. hirta was active against MM96L cells and very strongly active against HeLa cells.
c) E. drummondii had a lesser effect against MM96L than the other two samples, and inhibited HeLa cells only at the highest concentration tested.
d) NFF normal fibroblasts were severely affected at the 1/5 dilution, but only mildly affected at the other dilutions. For example, at a dilution of 1/25, there was mild inhibition of NFF cells (rating 2), but severe inhibition of MM96L cells (rating 4). At a dilution of 1/125, no effect was observed against NFF cells (rating 0), but severe inhibition of MM96L cells (rating 4) was observed for one sample, and milder inhibition (rating 1) with the duplicate sample). HACat cells, which could be considered as representative of normal keratinocytes, were only inhibited at the highest concentration.

At high concentrations of E. peplus sap, it appeared that there was direct killing of MM96 cells. However, at lower concentrations (down to a dilution of 1/625), although no growth inhibition was observed, the surviving cells were dendritic, and had the appearance of normal melanocytes. Without wishing to be limited to any proposed mechanism, it appears that E. peplus sap may contain at least one agent which promotes differentiation, rather than directly cytotoxic agents which damage DNA.

EXAMPLE 2

Effect of Heat or Acetone Treatment on Activity of Euphorbia Sap

The experiment described in Example 1 was repeated for E. peplus and E. hirta by a different person, using different cell line preparations, different plant samples and a different rating scale.

The samples were either prepared as described in Example 1, or were subjected to treatment with heat or acetone. Undiluted extracts of plant sap were heated at 95° C. for 15 minutes. For the acetone treatment, 40 $\mu$l extract was suspended in 400 $\mu$l acetone, and the tube shaken on a vortex mixer. Contents were centrifuged at 10,000 g for 3 minutes and the supernatant (acetone-soluble fraction) removed to a separate tube. Both the pellet and supernatant were left in open tubes at room temperature in the fume hood overnight with exhaust fan operating to evaporate the residual acetone.

The results are shown in Tables 7 to 9, in which +++ indicates no effect, and − indicates 100% cell death. "C" indicates that the culture was contaminated. Using this rating scale the results were even more striking than in Example 1, with strong inhibitory activity being observed up to a dilution of 1:3125. However, some growth inhibition of NFF cells was seen in this experiment.

Neither heat nor acetone affected the anti-tumour activity significantly. With acetone treatment, most activity was found in the pellet, particularly in the case of E. hirta, though some activity was also present in the soluble fraction. This suggests that the compounds responsible are not protein in nature, and that at least one component may be a lipid.

TABLE 7

MM96L

| | Dilution | | | | | | | | | |
|---|---|---|---|---|---|---|---|---|---|---|
| | Sample 1 | | | | | Sample 2 | | | | |
| Sample | 1/5 | 1/25 | 1/125 | 1/625 | 1/3125 | 1/5 | 1/25 | 1/125 | 1/625 | 1/3125 |
| E. peplus | − | − | ± | ± | ± | − | − | ± | + | + |
| E. hirta | − | ++ | ++ | +++ | +++ | | | | | |
| E. hirta heat | ± | + | + | +++ | +++ | | | | | |
| acetone soluble E. peplus | ± | + | + | +++ | +++ | | | | | |
| acetone soluble E. hirta | ± | ++ | +++ | +++ | +++ | | | | | |
| acetone precipitate E. peplus | − | + | + | +++ | +++ | | | | | |
| acetone precipitate E. hirta | − | −/± | ++ | +++ | +++ | − | − | ++ | +++ | +++ |
| E. peplus heat | − | + | +/++ | +/++ | +/++ | − | + | ++ | ++ | ++ |

TABLE 8

NFF

| | Dilution | | | | | | | | | |
|---|---|---|---|---|---|---|---|---|---|---|
| | Sample 1 | | | | | Sample 2 | | | | |
| Sample | 1/5 | 1/25 | 1/125 | 1/625 | 1/3125 | 1/5 | 1/25 | 1/125 | 1/625 | 1/3125 |
| E. peplus | − | + | c | +/++ | ++ | − | c | + | ++ | ++ |
| E. hirta | − | + | + | + | ++ | − | + | ++ | ++ | ++ |
| E. hirta heat | + | + | ++ | ++ | ++ | | | | | |
| acetone soluble E. peplus | ± | ++ | ++ | ++ | ++ | | | | | |
| acetone soluble E. hirta | + | ++ | ++ | ++ | ++ | | | | | |
| acetone precipitate E. peplus | ± | + | + | ++ | ++ | | | | | |
| acetone precipitate E. hirta | − | ± | + | ++ | + | | | | | |
| E. peplus heat | − | + | ++ | + | ++ | | | | | |

TABLE 9

HeLa Cells

| Sample | 1/5 | 1/25 | 1/125 | 1/625 | 1/3125 |
|---|---|---|---|---|---|
| E. peplus | ± | + | +++ | +++ | +++ |
| E. hirta | − | +++ | +++ | +++ | +++ |
| E. hirta heat | + | ++ | +++ | +++ | +++ |
| acetone soluble E. peplus | +++ | +++ | +++ | +++ | +++ |
| acetone soluble E. hirta | +++ | +++ | +++ | +++ | +++ |
| acetone ppte E. peplus | ++ | ++ | +++ | +++ | +++ |
| acetone ppte E. hirta | ± | +++ | +++ | +++ | +++ |
| E. peplus heat | − | +++ | +++ | +++ | +++ |

EXAMPLE 3

Further Tests Using E. peplus

Since E. peplus is the most abundant of the three plants tested in these studies, further experiments utilised extracts from this species. This is not to be taken to imply that activity is not present in the other two species.

Example 2 was repeated, using MM229 and MM220 human malignant melanoma cells and B16 mouse malignant melanoma cell lines, in addition to NFF and MM96L cells. Assays were performed in duplicate, using addition of an equivalent amount of water as a control, and dilutions of the pellet and supernatant fractions after acetone treatment from 1/20 to 1/12500. The results are summarised in Table 10.

TABLE 10

| Sample | H₂O Control | DILUTION | | | | | | | | | |
|---|---|---|---|---|---|---|---|---|---|---|---|
| | | 1/20 | 1/100 | 1/500 | 1/2,500 | 1/12,500 | 1/20 | 1/100 | 1/500 | 1/2,500 | 1/12,500 |
| NFF pellet | +++ | + | +++ | +++ | +++ | +++ | +/++ | +++ | +++ | +++ | +++ |
| NFF supernatant | +++ | + | +++ | +++ | +++ | +++ | + | +++ | +++ | +++ | +++ |
| MN96L pellet | +++ | − | + | +/++ | +++ | +++ | − | ++ | +++ | +++ | +++ |
| MM96L supernatant | +++ | ± | ++ | ++ | ++ | ++ | − | + | ++ | +++ | +++ |
| Hela pellet | +++ | − | + | ++/+++ | +++ | +++ | − | ++ | ++ | +++ | +++ |
| Hela supernatant | +++ | − | ± | ++ | ++ | ++ | − | ± | ++ | +++ | +++ |
| MM229 pellet | ++ | − | + | + | ++ | ++ | − | + | ± | ++ | ++ |
| MM229 supernatant | ++ | − | + | +/++ | + | ++ | ++ | + | ++ | + | + |
| MM220 pellet | ++ | − | ++ | ++ | ++ | − | + | ++ | ++ | ++ | ++ |
| MM220 supernatant | ++ | − | + | ++ | ++ | −− | − | ++ | ++ | ++ | ++ |
| B16 pellet | ++ | − | − | ++ | ++ | − | − | ++ | ++ | ++ | ++ |
| B16 supernatant | ++ | ++ | ++ | ++ | ++ | ++ | ++ | ++ | ++ | ++ | ++ |

The results confirm those obtained in Example 2. At a dilution of 1/100 to 1/50 there was no effect on NFF cells, but significant inhibition of MM96L cells was observed. The melanoma cells surviving at these dilutions had the appearance of normal melanocytes. Inhibition of the other two human melanoma cell lines and of the mouse melanoma cell line was also observed.

Similar results were obtained using Merkel cell carcinoma (MCC 16) or squamous cell carcinoma (Colo 6) cells. The results are shown in Table 11.

Dendritic cell morphology was displayed by squamous cell carcinoma, even at 1 in 500,000 dilution. This extreme potency of the crude extract was also evident for Merkel cell inhibition, which was also still evident at 1 in 500,000 dilution.

TABLE 11

Effect of crude sap from *E. peplus* on Merkel cell carcinoma (MCC16) and squamous cell carcinoma (Colo16) cell numbers.

| Cell line | Sample | 1/50 | 1/500 | 1/5,000 | 1/50,000 | 1/500,000 |
|---|---|---|---|---|---|---|
| Colo16 | Solvent (control) crude | +++ | +++ | +++ | +++ | +++ |
| | *E. peplus* sap | − | ++d* | +++d* | +++d* | +++d* |
| MCC16 | Solvent (control) crude | +++ | +++ | +++ | +++ | +++ |
| | *E. peplus* sap | − | ±* | + | + | ++ |

Scale:
+++ = no effect,
− = complete cell death
*d = indicates change to dendritic morphology of the cells; dendricity not recorded for MCC16 ratings.

EXAMPLE 4

Ethanol Extract of *E. peplus*

A fresh preparation of sap from *E. peplus* was subjected to extraction with 95% aqueous ethanol. Ethanol was removed from the soluble fraction after extraction by vacuum centrifugation, and the fraction was reconstituted to its original volume in tissue culture medium (RPMI1640) containing 5% foetal calf serum and antibiotics. The pellet remaining after ethanol extraction was dried by vacuum centrifugation and reconstituted to its original volume in tissue culture medium as described above. The crude sap (C), the soluble fraction (S) and the pellet (P) were tested as described above against NFF cells, the melanoma cell lines MM96L, MM537, MM229 and MM2058, and also against the colon cancer cell line LIM1215 and the lung cancer cell line A549. Assays were performed in triplicate, and were assessed after four days culture following addition of the sample. The results are shown in Table 12, in which + indicates normal appearance of cells, ++ indicates a possible increase in cell numbers, and − indicates cell death.

TABLE 12

| | Dilution | | | | | | | | | | | |
|---|---|---|---|---|---|---|---|---|---|---|---|---|
| | 1/20 | | | 1/100 | | | 1/500 | | | 1/2,500 | | |
| Cell line | C | S | P | C | S | P | C | S | P | C | S | P |
| NFF | − | +/− | + | + | + | + | + | + | + | + | + | + |
| MM 96L | − | +/− | +/− | +/− | +/− | +/− | +/− | +/− | +/− | +/− | + | + |
| MM 537 | − | − | + | +/− | + | + | + | + | + | + | + | + |
| MM 229 | − | +/− | + | +/− | + | + | + | + | + | + | + | + |
| MM 2058 | − | +/− | +/− | +/− | + | + | + | + | + | + | + | + |
| Hela | − | +/− | | +/− | + | + | + | + | + | + | + | + |
| LIM 1215 | − | − | + | − | + | + | + | + | + | + | + | ++ |
| A 549 | − | − | +/− | +/− | − | +/− | +/− | +/− | + | +/− | +/− | + |

The results obtained were consistent with those of the previous experiments. Again at low doses the MM96L cells had a dendritic appearance. All of the tumour cell lines as well as the normal fibroblast cell line NFF were killed by the crude sap and by the soluble fraction obtained by ethanol extraction at a dilution of 1/20. It appeared that the majority of the activity partitioned to the ethanol-soluble fraction. The lung cancer cell line A459 appeared to be particularly susceptible, being affected at a dilution of up to 1/2500 by both the crude sap and by the soluble fraction.

EXAMPLE 5

Reporter Assay for Gene Expression in Transfected MM96L Malignant Melanoma Cell Line

*E. peplus* sap in phosphate-buffered saline diluent was added to wells containing MM96L cells or the breast cancer cell line MCF7 transfected with a construct consisting of the sheep metallothionein promoter, upstream of a β-galactosidase reporter gene which had been substituted for the metallothionein gene. The assay thus becomes a measure of gene expression and in particular, of potential transcription, translation and expression of the metallothionein gene. Cells were treated with 4 extract in microtitre plates for 20 hr, 100 μM ZnSO$_4$ was added and the plates incubated for a further 5 hr, and the medium was removed. β-galactosidase activity was then measured by incubation of the cells for 1–2 h at 37° C. with a chromogenic substrate. This assay is used as a sensitive test for transcriptional activation of genes.

Figure 1:
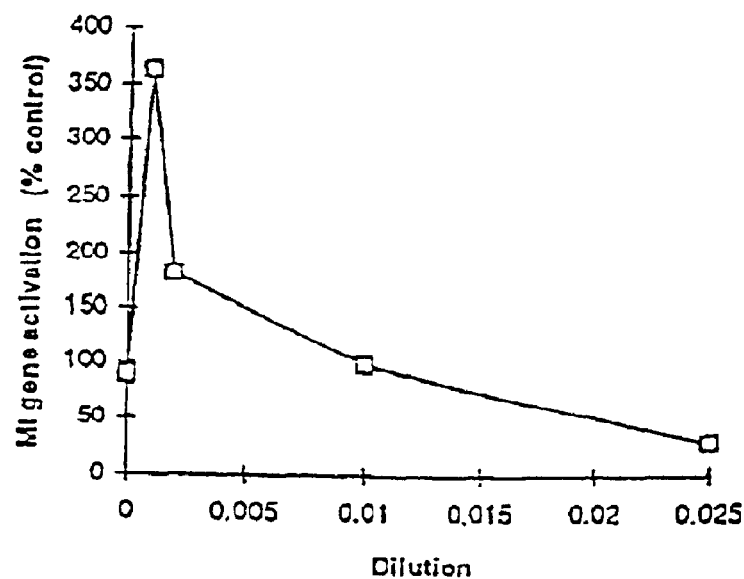
FIG. 1 shows the effect of *E. peplus* sap on metallothionein gene activation, measured by detecting the activity of β-galactosidase using a chromogenic substrate.

The results are shown in FIG. 1.

This shows that there was a marked stimulation of metallothionein gene activation, as measured by increased β-galactosidase reporter gene expression, which surprisingly became more evident as the sample further was diluted. The mechanism by which E. peplus sap mediates this effect is not understood. Whereas known drugs specific for inhibition of histone deacetylase activity demonstrate increasing expression of the reporter gene with increasing concentration of drug, E. peplus exhibits an inverse dose response. However, the results indicate that this assay can be used to monitor purification of the active agents(s) in E. peplus sap or the plant itself.

Figure 2:
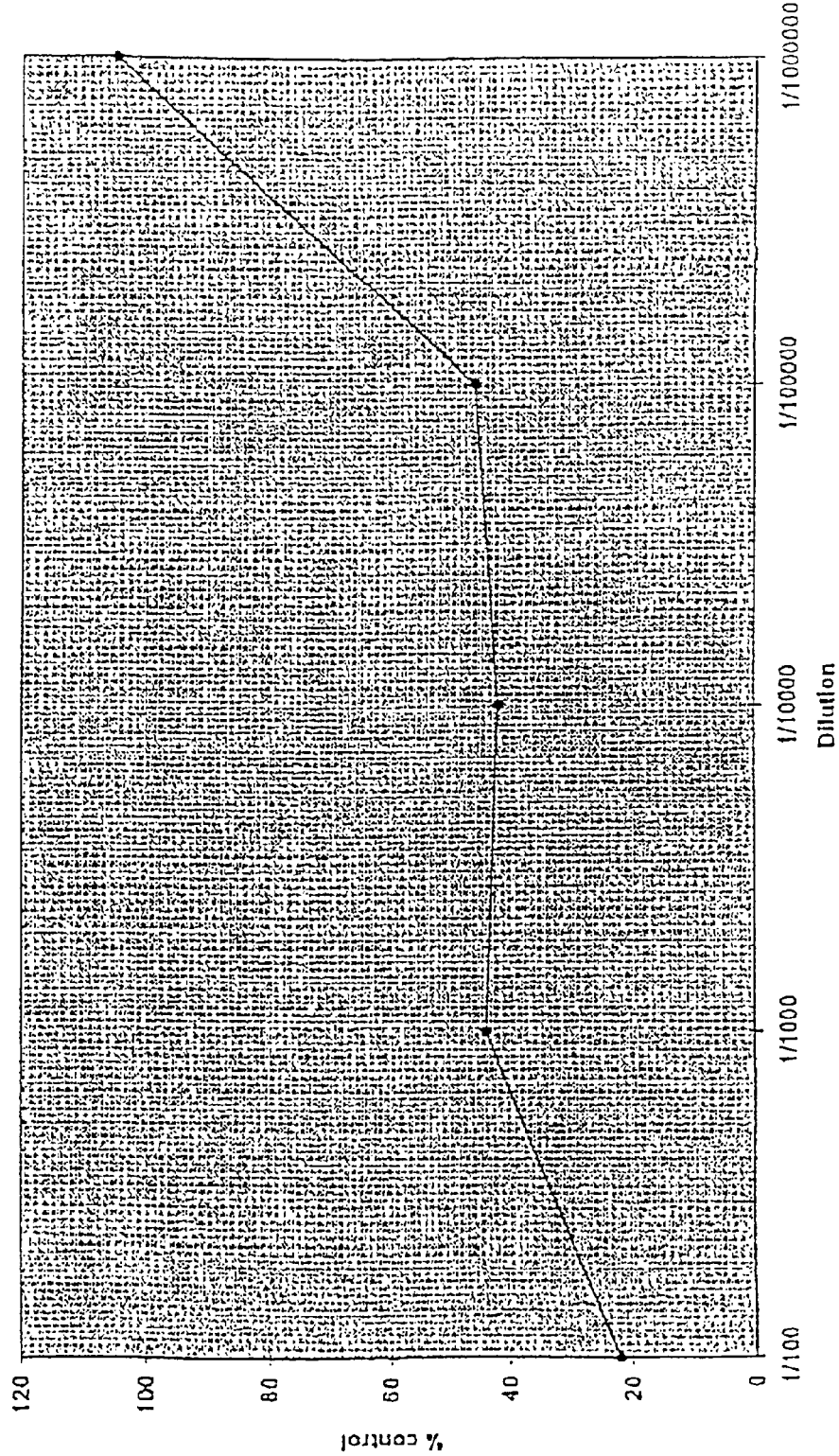
FIG. 2 shows the proliferation of MCF7 breast cancer cells grown in microtitre wells in the presence of *E. peplus* sap for 7 days (expressed as a percentage of control values).

The metallothionein protein has antioxidant activity, and is implicated in a protective role against heavy metal-induced cancers. Activation of the metallothionein promoter occurred at concentrations of E. peplus sap too low to effect direct cell killing, except for the extremely sensitive breast cancer cell line MCF7 (FIG. 2). The change in appearance of MM96L melanoma cells to the dendritic morphology of normal melanocytes at these dilutions possibly implicates the metallothionein gene in these effects.

EXAMPLE 6

Subfractionation of Ethanol-Soluble Extract

The soluble fraction obtained by extraction with 95% ethanol, performed as in Example 4, was subjected to isocratic reverse-phase high-performance liquid chromatography (RP-HPLC).

100 μl of crude extract was dissolved in 1 ml 95% ethanol and periodically shaken at 4° C. overnight. The extract was centrifuged at 10,000×g for 4 minutes, and the supernatant was removed and dried by vacuum centrifugation. The solids were reconstituted in 100 μl running buffer centrifuged briefly, and the soluble material applied to a Brownlee Aquapore RP-300 column (C8), 220×4 mm, with a 30×4 mm RP-300 guard column.

Figure 3:
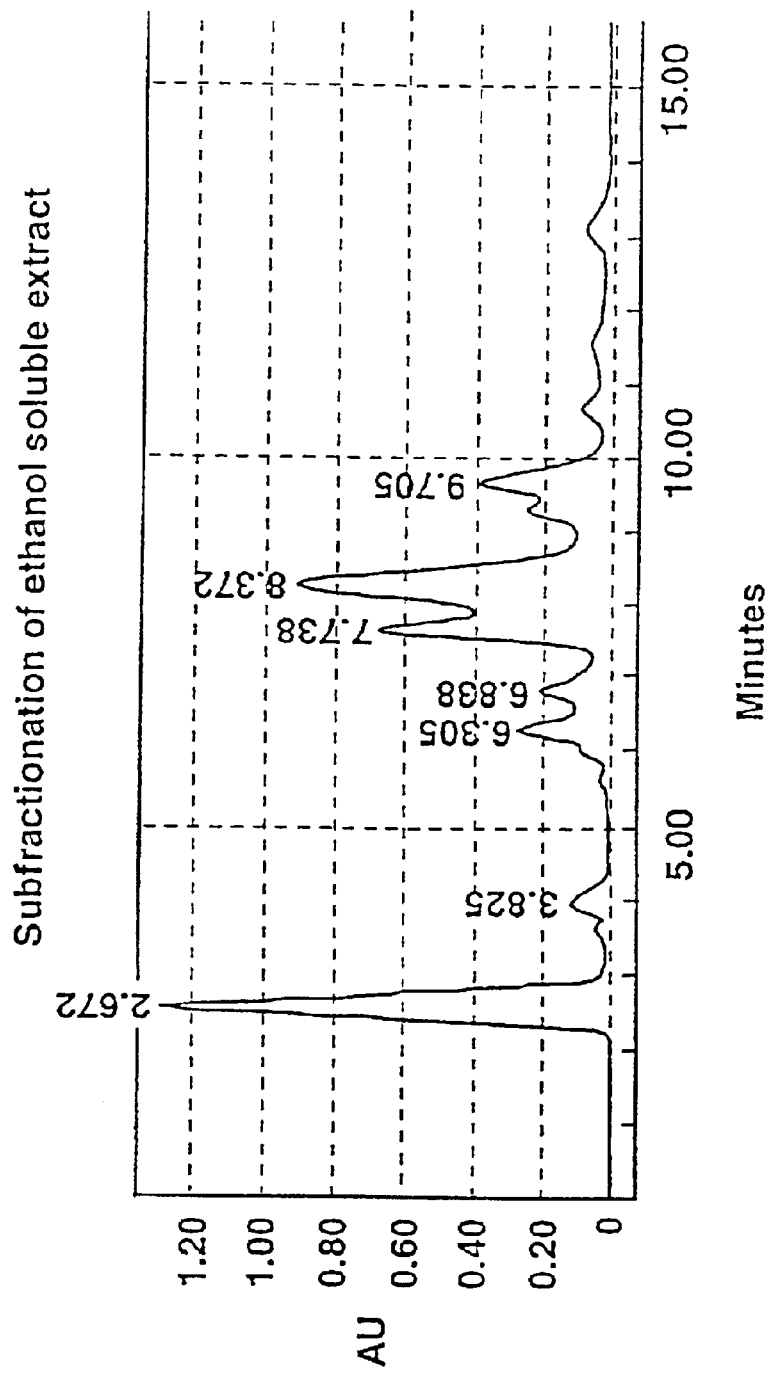
FIG. 3 shows the absorbance profile at 195 mm, following RP-HPLC sub-fractionation of an ethanol-soluble extract of *E. peplus* sap.

The running buffer was acetonitrile:water 50:50 (V/V), and the flow rate was 0.75 ml/mn. Fractions were collected at 0.5 min intervals, and the absorbance profile at 195 mn was monitored. The absorbance profile is shown in FIG. 3.

Fractions were dried by vacuum centrifugation, reconstituted in 500 μl PBS, and assayed against MM96L cells and in the metallothionein reporter assay as described above. Fractions 13 to 28 all induced complete reversion of MM96L cells to a dendritic appearance, but cell death was not observed. The effect was much more striking in the reporter assay, in which activity was still observed at a dilution of 1/10,000 (i.e. at a final concentration in the culture of 1/100,000).

In addition to the foregoing results, the inventor has found that following ultracentrifugation, activity against MM96L cells is found both in the supernatant and in the pellet, and that activity cannot be removed by passing a sample through a molecular weight cut-off membrane. In addition to the cell lines tested above, proliferation of cells of the MCF7 breast cancer cell line was inhibited by E. peplus sap at a final dilution of up to 1/100,000. Cell numbers were assessed using the bicinchoninic acid reagent (Pierce). Results are shown in FIG. 2.

EXAMPLE 7

Solvent Fractionation

Further solvent fractionation of the crude latex of E. peplus was effected by a series of solvents of increasing polarity. To 1 ml crude latex was added 20 ml diethyl ether in a centrifuge tube. The tube was shaken and centrifuged at 5000 g for 5 minutes to partition the layers. The diethyl ether upper layer was removed and the procedure repeated twice. The ether fractions were combined, concentrated to dryness on a rotary evaporator and reconstituted in 1 ml DME for bioassay. In a similar manner, the residue was extracted with ethyl acetate, followed by methylene chloride. The initial ether extract obtained the majority of the activity as measured by decrease in cell numbers of MCF7 breast cancer cells and reversion to a dendritic appearance. However, activity was also demonstrated from the fractions derived from the ethyl acetate and methylene chloride layers. No activity was seen in the final water-soluble (aqueous) fraction. The results are summarised in Table 13.

TABLE 13

| Cell line* | Sample | 1/50 | 1/500 | 1/5,000 | 1/50,00 | 1/500,000 |
|---|---|---|---|---|---|---|
| NFF | crude E. peplus latex | − | ± | + | + | + |
| | diethylether fraction | − | ± | + | + | + |
| | ethyl acetate fraction | ± | + | + | + | + |
| | methylene chloride fraction | + | ± | + | + | + |
| | aqueous fraction | + | + | + | + | + |
| HT144 | crude E. peplus latex | − | − | + | + | + |
| | diethylether fraction | − | ± | + | + | + |
| | ethyl acetate fraction | ± | + | + | ++ | ++ |
| | methylene chloride fraction | + | + | ++ | ++ | ++ |
| | aqueous fraction | + | ++ | ++ | ++ | ++ |
| MCF7 | crude E. peplus latex | − | − | ± | ± | ± |
| | diethylether fraction | − | − | ± | ± | ± |
| | ethyl acetate fraction | − | ± | ± | ± | ± |
| | methylene chloride fraction | ± | ± | ± | + | + |
| | aqueous fraction | + | + | + | + | + |

*= NFF: normal fibroblasts, HT144: human melanoma, MCF7: human breast cancer

CMV promoter activity was assayed in HeLa cells infected with a replication-deficient adenovirus construct, in which the Ela gene had been replaced by the CMV promoter driving β-galactosidase. The results, shown in Table 14, are expressed as a percentage of the control values of infected, untreated cells.

TABLE 14

| | Dilution | | |
|---|---|---|---|
| Sample | 1/50 | 1/500 | 1/5,000 |
| crude E. peplus latex | 170 | 175 | 400 |
| diethylether fraction | 240 | 250 | 345 |
| ethyl acetate fraction | 630 | 550 | 360 |

TABLE 14-continued

| Sample | Dilution | | |
|---|---|---|---|
| | 1/50 | 1/500 | 1/5,000 |
| methylene chloride fraction | 746 | 420 | 170 |
| aqueous fraction | 180 | 100 | 100 |
| solvent control* | 100 | approx 100 | 100 |

*ethylene glycol dimethyl ether (DME)

The results obtained are qualitatively similar to those seen with other differentiation-inducing agents, such as histone deacetylase inhibitors or butyrate, albeit with more potent activity than seen with these agents. The lower promoter activity observed with the crude and the diethylether extracts at higher concentrations probably reflects cell killing effects against HeLa cells seen at those concentrations.

In a further solvent fractionation experiment, the crude sap was partitioned between methanol:water (17:3) and n-hexane, a solvent partition expected on the basis of previous reports to separate diterpenes (polar phase) from the triterpenes (heptane phase) (Evans and Kinghorn 1977). Unexpectedly, however, activity was detected in both phases, suggesting that the active principles behave anomalously in this system.

Another solvent fractionation approach was suggested by the need to clarify samples prior to HPLC analysis. The crude latex was mixed with ethanol to 70–95% and shaken overnight at 4° C. The mixture was centrifuged at 1,000 g for 10 min, and the supernatant was removed and concentrated to approx one third the original volume of crude sap. To the concentrate was added 100% acetonitrile to 30–60%. The resulting white precipitate was removed by centrifugation at 12,000 g for 10 minutes. The supernatant was enriched in macrocyclic diterpenes (jatrophanes and pepluane), as determined by TLC and mass spectroscopy. This observation points the way to a suitable large scale process for enrichment of the active principles.

EXAMPLE 8

Further Activity-Guided Subfractionation of the Ethanol-Soluble Extract

Figure 4:
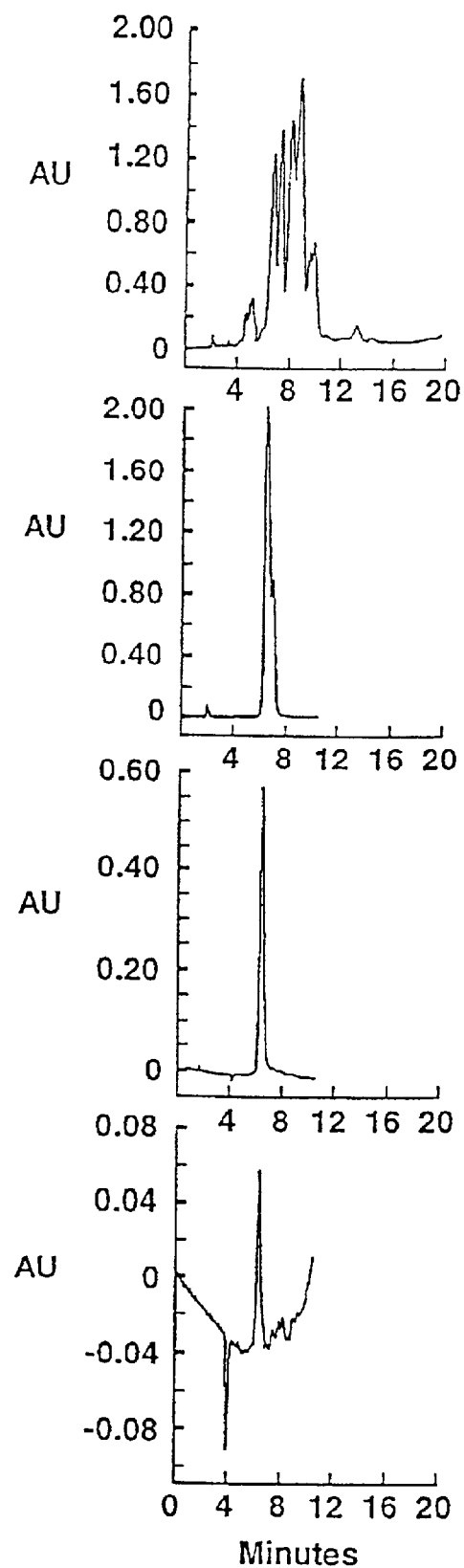
FIG. 4 shows the results of repeated RP-HPLC chromatography of fraction 14 from FIG. 3.
Figure 5:
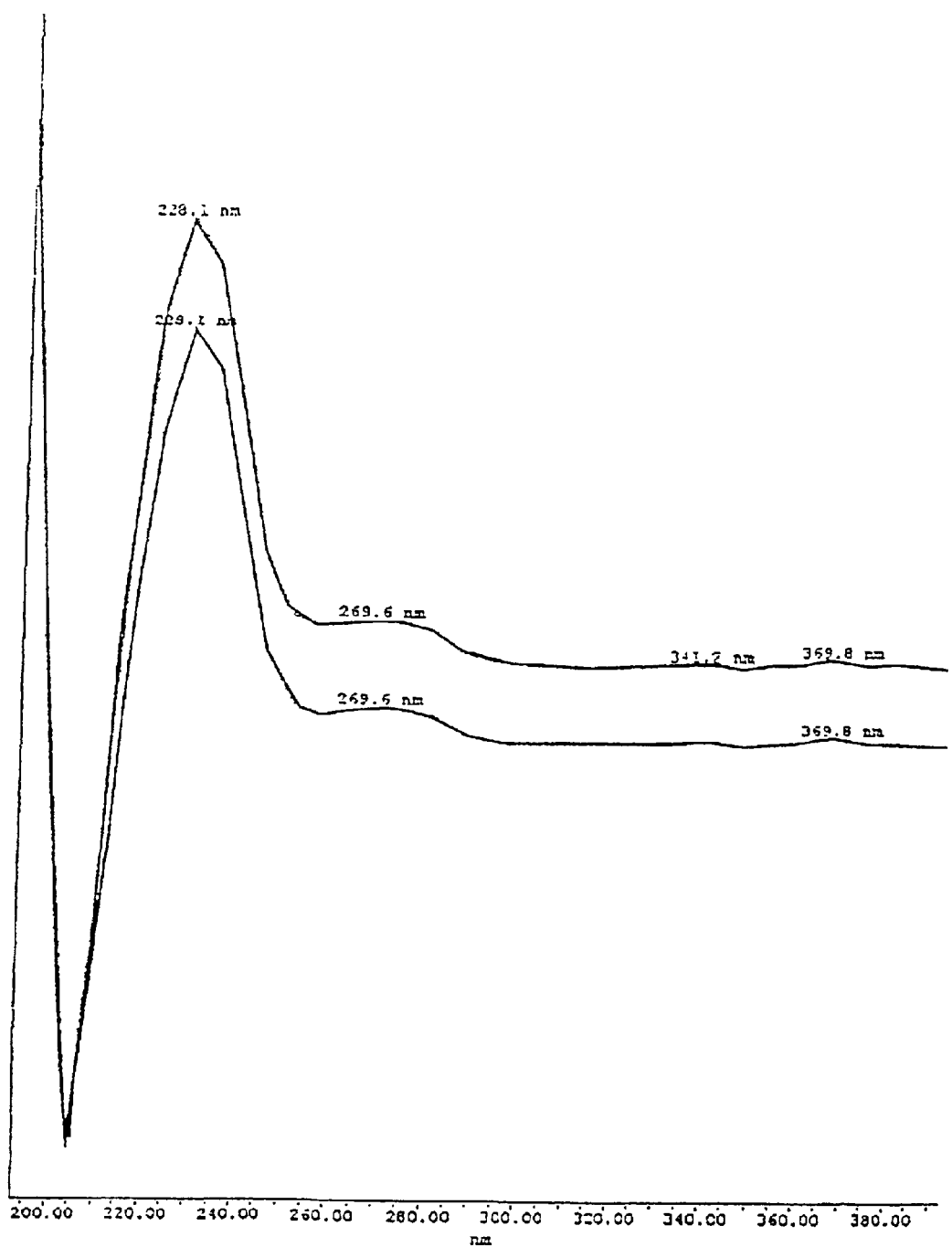
FIG. 5 shows the constant diode array spectrum of the peak from FIG. 4.

Fractions 14 and 15 from the HPLC subfractionation described in Example 7 and FIG. 3 were further purified by repeated chromatography, selecting the dominant symmetrical peak with constant diode array spectra (e.g. fractions 14 and 15; results for fraction 14 are shown in FIGS. 4 and 5). Activity of the purified fractions in causing reversion of MM96L to the dendritic appearance was confirmed by cell assay.

Figure 6:
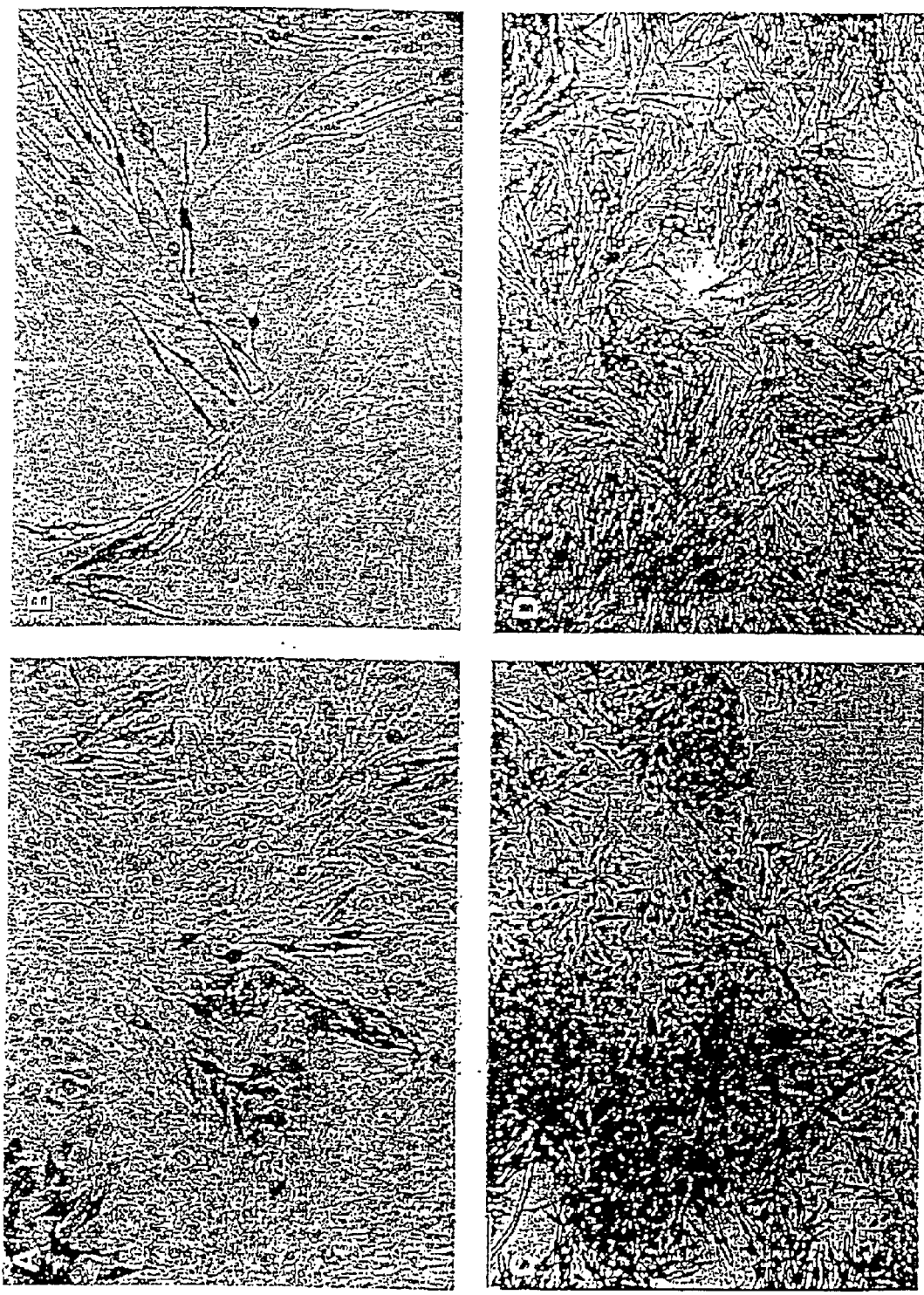
FIG. 6 shows the results of treatment of MM96L melanoma cells with Fraction 15 from Example 7. Cells are stained with antibody TRP-1, directed against the cytoskeleton A,B: 4 days, C,D: 21 days

The features of the change to MM96L cells after the addition of Fraction 15 are shown in FIG. 6. Cells were visualised as photomicrographs, using an antibody coupling procedure. The first antibody, a mouse monoclonal directed towards tyrosinase-related protein 1 (TRP-1), was detected with a second antibody, sheep anti-mouse-alkaline phosphatase conjugate, using bromo-chloro-indolyl phosphate and nitroblue tetrazolium (BCIP/NBT) as developing substrates. After four days of incubation (FIGS. 6A and 6B) there was a marked reduction in the number of melanoma cells and a pronounced change in their morphology. The cells had reverted to a long, spindly (dendritic) appearance, characteristic of normal mature melanocytes. All cells in the field appeared to have adopted this altered morphology, which is surprising given the heterogeneous nature of the MM96L cell population. After 21 days of incubation, the treated cells were seen to align somewhat parallel to one another in clusters, as shown in FIGS. 6C and 6D, a characteristic of normal, mature melanocytes. Similar features have been observed with all dendritic cell-inducing fractions from E. peplus, including the crude sap.

Electrospray mass spectroscopic analyses for fractions 14 and 15 indicated the presence of 2,5,7,14-tetraacetoxy-3-benzoyloxy-8,15-dihydroxy-9-nicotinoyloxyjatropha-6(17),11E-diene (jatrophane 5, Jakupovic et al, 1998a) with an m/z of 780 (calculated 779.315). Nuclear magnetic resonance (NMR) analysis, using 1D NMR, on fraction 14 gave down-field signals between 7 and 9.4 ppm which are consistent with a pyridine-like moiety, as is present in the nicotinoate group at ring position 9. Also, a trans double bond was evidenced by the large coupling constant at 5–6 ppm, in agreement with the 11, 12 internal double bond in the jatrophane ring structure. Also identified in fraction 14 by electroscray in the negative ion mode was 2,5,7,9,14-pentaacetoxy-3-benzoyloxy-8,15-dihydroxy-jatropha-6(17),11E-diene (jatrophane 6, Jakupovic et al, 1998a), with m/z 716 (calculated 716.304), 673 (M-ketene), 656 (M-AcOH).

Fraction 15 contained 2,3,5,7,15-pentaacetoxy-9-nicotinoyloxy-14-oxojatropha-6(17),11E-diene (jatrophane 1, Jakupovic et al, 1998a) with m/z 597 (M-ketene-AcOH). Thus, by spectroscopic analysis, the early-eluting fractions at 7–7.5 minutes on HPLC with cell killing and dendritic activity contained a mixture of jatrophanes 5, 6, and 1. This result is consistent with the behaviour of HPLC fractions 14 and 15 when chromatographed on HPTLC, using toluene-:acetone 9:1 as the developing solvent. UV-positive spots did not move from the origin, $R_f$ 0.0 (approx), in contrast to later-eluting fractions (e.g. fractions 20–22, $R_f$ 0.3–0.5). This indicates the relatively polar behaviour of jatrophanes 5, 6, and 1, in comparison to jatrophanes 3, 2 and 4, as demonstrated by chromatography on HPTLC, using either toluene:acetone 9:1 or hexane:ethyl acetate 4:1 as developing solvents. These results are similar to those obtained by Jakupovic et al, 1998a, using petrol:methyl-tert-butyl ether (1:1) as the developing solvent, e.g.: jatrophane 5: $R_f$ 0.04, jatrophane 6: $R_f$ 0.10 (3X), and jatrophane 1: $R_f$ 0.11. There was no evidence in the mass spectroscopic data from the early HPLC fractions of the presence of ingenane derivatives (see later), or other components reported from the literature and presented in Table 1, in E. peplus crude extracts.

EXAMPLE 9

Biological Activity-Guided Purification of Crude and Ether-Soluble Extracts on Thin Layer Chromatography (TLC) and High Performance Thin Layer Chromatography (HPTLC)

Figure 7:
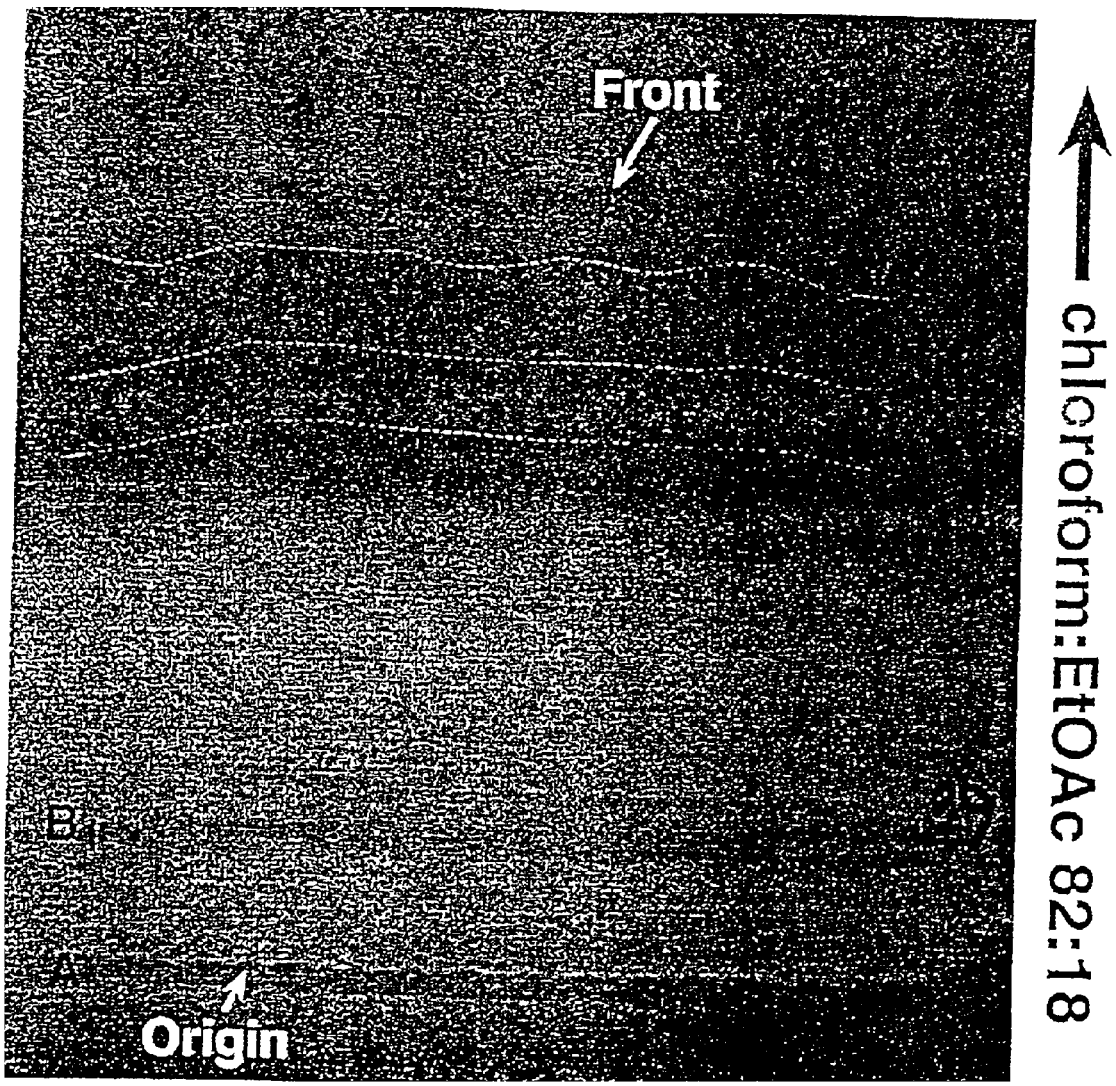
FIG. 7 shows the results of thin layer chromatography of the ether-soluble fraction from Example 6 using chloroform-:ethyl acetate (82:18) as the developing solvent.

(a) The ether-soluble fraction, prepared as in Example 7, was reconstituted in ethylene glycol dimethyl ether (DME) and chromatographed on 20×20 cm silica gel plates, using chloroform:ethyl acetate (82:18) as the developing solvent (FIG. 7). The plate was viewed on a UV light box and the UV positive bands were identified, excised from the gel, eluted with DME, and tested for inhibitory activity and morphology reversal against MM96L melanoma cell line. By slicing the whole gel into UV and non-UV absorbing fractions, it was demonstrated in preliminary experiments that activity was associated with the UV-absorbing bands. Staining the side strips of the gel with 0.1% iodine in chloroform revealed other iodine strongly positive bands.

However, these were found to possess negligible activity. UV-absorbing bands at Rf 0.0 (A), Rf 0.16–0.18 (B1), Rf 0.22–0.24 (B2), Rf 0.73–0.80 (C), Rf 0.80–0.96 (D) were biologically active, with observable decrease in cell numbers and complete reversion to dendritic cell appearance at 1/5,000 dilution.

Figure 8:
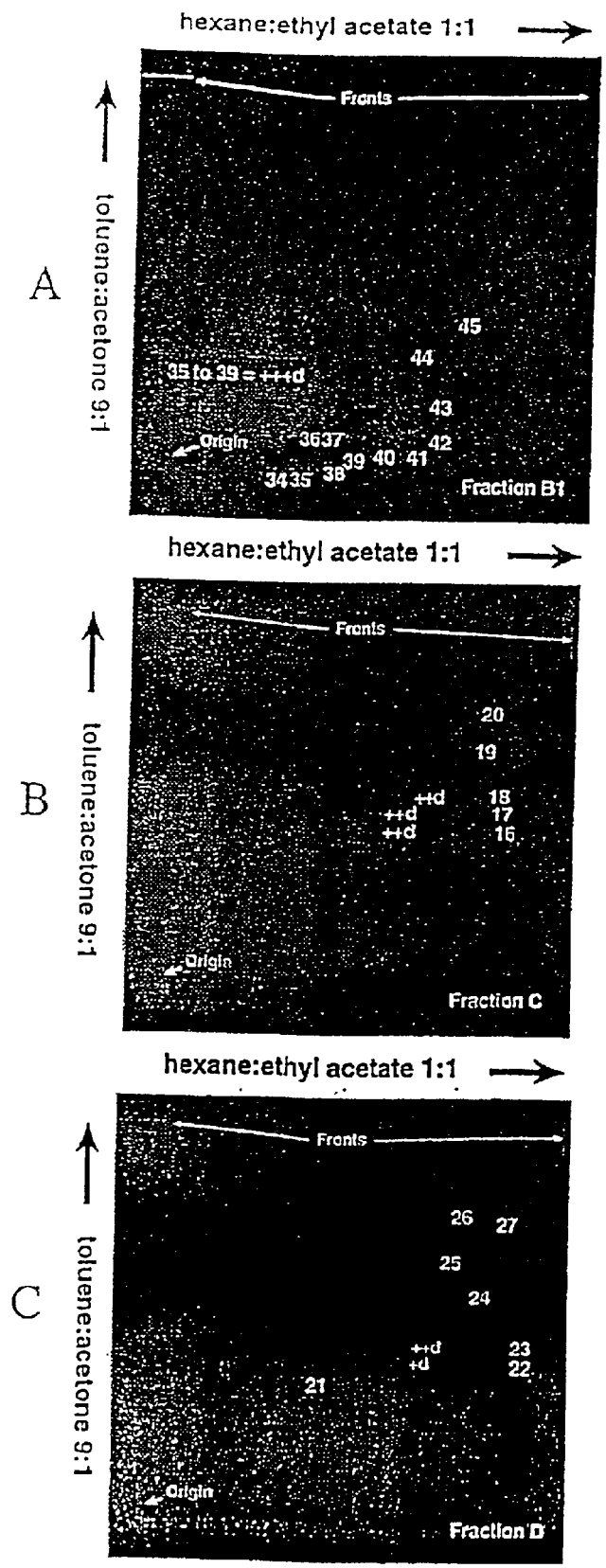
FIG. 8 shows the results of further purification by 2-dimensional TLC on silica gel, using hexane:ethyl acetate (1:1) in the first dimension, and toluene:acetone (9:1) in the second dimension.

Zones B1, C and D were further purified by chromatography on silica gel 60 plates, using a two-dimensional solvent system with hexane:ethyl acetate (1:1) in the first dimension and toluene:acetone (9:1) in the second dimension (FIGS. 8A to 8C respectively). UV-absorbing spots with inhibitory activity towards MM96L of greater than 30% of cell numbers and with complete reversion to dendritic cell appearance at 1/500 dilution are indicated on the figures.

The strongly UV-absorbing spots 22 and 23 derived from zone D (see FIG. 8C) were excised from the gel, eluted with DME and dried by vacuum centrifugation. Mass spectroscopic analysis of fractions 22 and 23 revealed the presence of 5,8,9,10,14-pentaacetoxy-3-benzoyloxy-15-hydroxypepluane, m/z 639.5 [M-AcOH]$^+$, i.e. pepluane.

(b) Whole crude sap was chromatographed on 10×10 cm HPTLC silica gel 60 plates with concentrating zones (Merck Cat No. 013748.1000), using toluene:acetone (9:1) as the developing solvent, as shown in FIG. 9. The UV-positive zones (1, R$_f$ 0.14; 2, R$_f$ 0.23; 3, R$_f$ 0.49; 4, R$_f$ 0.54; 5, R$_f$ 0.57; 6, R$_f$ 0.63; and 7, R$_f$ 0.73) were excised from the gel and eluted with DME/diethyl ether. The fractions were tested against MM96L as described above, and fractions 1, 3, 4, 5 and 6 were demonstrated to possess cell inhibitory activity and cell reversion activity. These fractions were separately chromatographed on HPTLC plates using hexane:ethyl acetate (4:1) as the developing solvent, yielding UV positive bands A, R$_f$ 0.17; B, R$_f$ 0.24; C, R$_f$ 0.42; D, R$_f$ 0.48; E, R$_f$ 0.52; F, R$_f$ 0.58; G, R$_f$ 0.62 (FIG. 10) and H, R 0.02 (FIG. 11). All fractions except G (iodine positive, see FIG. 10) were active against MM96L cells, in terms of cell growth inhibition and reversion to complete dendritic morphology, at 1 in 5000 dilution.

Mass spectroscopic analyses of fractions A–F (B missing) and H are shown in Table 15, with a tentative assignment of compounds from the known molecular mass ions of the published constituents of *E. peplus*:

TABLE 15

Mass spectroscopic analysis of HPTLC Fractions

Fraction m/z, Relative Abundance (%) and tentative assignment

| | |
|---|---|
| A | 495.2357 (100) [C$_{27}$H$_{36}$O$_7$Na$^+$(ingenol acetate)], 433.3799 (51), 579.2916 (39) [pepluane-2AcOH]$^+$, 679.2754 (16), 691.4046 (16) |
| B | N.D. |
| C | 579.2846 (100) [pepluane-2AcOH]$^+$, 691.4073 (50), 747.47 (8) [jatrophane 3-AcOH]$^+$, 803.53 (11) |
| D | 579.2827 (100) [pepluane-2AcOH]$^+$, 691.4025 (23), 715.3686 (38) [jatrophane 2-ketene]$^+$ |
| E | 437.2254 (100), 619.5287 (18), [jatrophane 4, 638-ketene + Na$^+$], 647.5615 (18) [jatrophane 4-2AcOH + Na$^+$] |
| F | 591.4996 (55), 619.5299 (100) [jatrophane 4, 638-ketene + Na$^+$], 647.5635 (77) [jatrophane 4-2AcOH + Na$^+$], 691.4183 (49) |
| H | 830.3216 (100) [jatrophane 3 + Na$^+$] | pepluane=5,8,9,10,14-pentaacetoxy-3-benzoyloxy-15-hydroxypepluane jatrophane 2=2,5,7,9,14-hexaacetoxy-3-benzoyloxy-15-hydroxy-jatropha-6(17),11E-diene jatrophane 3=2,5,14-triacetoxy-3-benzoyloxy-8,15-dihydroxy-7-isobutyroyloxy-9-nicotinoyloxyjatropha-6(17), 11E-diene jatrophane 4=2,5,9,14-tetraacetoxy-3-benzoyloxy-8,15-dihydroxy-7-isobutyroyloxyjatropha-6(17),11E-diene Thus, mass spectroscopy revealed a mixture of 20-acetyl-ingenol-3-angelate (fraction A), pepluane (fractions A, C & D) and jatrophanes 2 (fraction D) 3 (fractions C&H), and 4 (fractions E & F). $^1$H chemical shift data for fraction H are shown in Table 16.

TABLE 16

$^1$H Chemical Shift* Data for Fraction H

| H | ppm | Multiplicity |
|---|---|---|
| Indicative Jatrophane Ring Backbone Signals | | |
| 1α | 2.816 | brd |
| 1β | 2.056 | d |
| 3 | 5.918 | d |
| 4 | 3.731 | brd |
| 5 | 5.730 | brd |
| 7 | 5.390 | d |
| 8 (OH) | 2.948 | d |
| 9 | 4.971 | s |
| 11 | 6.145 | d |
| 12 | 5.640 | dd |
| 13 | 2.840 | cm |
| 14 | 5.110 | s |
| 15 (OH) | 3.645 | s |
| 16 | 1.489 | s |
| 17 | 4.438 | d |
| 17' | 4.788 | d |
| 18 | 1.052 | s |
| 19 | 1.152 | s |
| 20 | 1.353 | d |
| Ester Substituent Signals | | |
| Onic | 9.290 | brd |
| | 8.340 | ddd |
| | 8.805 | brdd |
| | 7.390 | brd |
| Onic | 9.079 | brd |
| | 8.202 | ddd |
| | 8.767 | brdd |
| | 7.327 | brd |
| OBz | 8.040 | AA' |
| | 7.403 | BB' |
| | 7.541 | C |
| OiBu | 1.972 | qq |
| | 0.912 | d |
| | 0.449 | d |
| | 0.450 | d |

*Chemical shifts are measured at 295K relative to chloroform at 7.24 ppm.

These assignments indicated the presence of a jatrophane ring structure as determined from DQF-COSY, NOESY and TOCSY two-dimensional spectra. The spectrum of Fraction H was consistent with the presence of Jatrophane 3 in two diastereomeric conformations (considered most likely), a mixture of two or more similarly substituted jatrophanes, or a new jatrophane with two nicotinate, one benzoate, and an iso-butyrate moiety. The likely ring confirmation was II, as per Jakupovic et al (1998a), with a J4,5 of approximately 6 Hz and strong NOE's between 5 and 8, and 4 and 7; with J7,8 and J8,9 practically zero—as evidenced by total lack of cross peaks in the DQF COSY spectrum. There were no signals consistent with the presence of any ingenol structure. The sample was retrieved from the magnet, and an aliquot demonstrated potent activity against MM96L, evidenced by complete cell death at 20 μg/ml, and complete reversion to a dendritic appearance at less than 20 pg/ml.

EXAMPLE 10

NMR Analysis

Fraction A was further purified by chromatography on HPTLC using hexane:ethyl acetate (4:1) as the developing solvent. As an adjunct to absorbance on a UV light box, a side strip was stained by spraying the gel with 70% phosphoric acid in methanol, and development by heating the gel with a hair drier revealed an intense blue band under UV light, separable from the major UV absorbing band. The unstained region equivalent to this band was excised, eluted with ether and dried by vacuum centrifugation. Approx. 1 mg of this material was accumulated from 4 ml latex. The material was subjected to NMR analysis, and subsequently bioassayed and demonstrated to be active in terms of reversion to complete dendritic morphology at 1 in $5\times10^6$ dilution, representing a 1 ng/ml final concentration. This material was identified by NMR as $C_{27}H_{36}O_7$, 20-acetyl-ingenol-3-angelate as shown in Table 17. This finding is consistent with the mass spectroscopic evidence presented in Table 15.

TABLE 17

NMR data obtained on bioactive fraction A2 to support 20-acetyl-ingenol-3-angelate chemical structure:

| $^1$H NMR | | | | $^{13}$C NMR | |
|---|---|---|---|---|---|
| H | ppm/multiplicity | # | C | Hz | [PPM] |
| 1 | 6.106 | 1 | 9 | 25933.898 | 206.2210 |
| 3 | 5.396 s | 2 | 26 | 21513.854 | 171.0737 |
| 5 | 3.875 d | 3 | 21 | 21165.912 | 168.3070 |
| 7 | 6.024 d | 4 | 23 | 17626.074 | 140.1589 |
| 8 | 4.076 | 5 | 2 | 17086.838 | 135.8710 |
| 11 | 2.4783 m | 6 | 6 | 17082.062 | 135.8330 |
| 12 | 2.222 ddd | 7 | 1 | 16614.730 | 132.1169 |
| 12' | 1.743 ddd | 8 | 7 | 16301.014 | 129.6223 |
| 13 | 0.681 m | 9 | 22 | 15976.620 | 127.0428 |
| 14 | 0.936 m | 10 | 4 | 10668.691 | 84.8352 |
| 16 | 1.033 s | 11 | 3 | 10395.504 | 82.6629 |
| 17 | 1.062 s | 12 | 5 | 9411.686 | 74.8398 |
| 18 | 0.952 d | 13 | 10 | 9059.148 | 72.0365 |
| 19 | 1.785 brs | 14 | 20 | 8404.062 | 66.8274 |
| 20 | 4.745 d | 15 | 8 | 5481.686 | 43.5892 |
| 20' | 4.467 d | 16 | 11 | 4841.115 | 38.4955 |
| 23 | 6.153 qq | 17 | 12 | 3911.906 | 31.1067 |
| 24 | 1.906 brs | 18 | ? | 3735.577 | 29.7045 |
| 25 | 1.996 brdd | 19 | 16 | 3585.756 | 28.5132 |
| 27 | 2.042 | 20 | 15 | 3018.427 | 24.0019 |
| 40H | 3.4308 | 21 | 13 | 2924.308 | 23.2535 |
| 50H | 3.514 d | 22 | 14 | 2892.863 | 23.0035 |
| | | 23 | 27 | 2655.734 | 31.1179 |
| | | 24 | 24 | 2612.189 | 20.7716 |
| | | 25 | 18 | 2171.913 | 17.2706 |
| | | 26 | 25 | 2007.760 | 15.9653 |
| | | 27 | 19 | 1698.690 | 15.6546 |
| | | 28 | 17 | 1951.372 | 15.5169 |

However, thee absence of 20-acetyl-ingenol-3-angelate from the mass spectra of the activity-guided purifications by HPLC, and in other TLC fractions apart from fraction A, indicates that this is not the only active fraction. Rather, jatrophanes 1–6 and pepluane are also implicated by deduction from the NMR and mass spectroscopic data. This is particularly true of fractions H as prepared by TLC (jatrophane 3 Na$^+$ m/z 830; see also 1D NMR results in Table 16) and fractions 13 and 14 as prepared by HPLC (jatrophane 5, m/z 779 and 1D NMR; jatrophane 6, m/z 716; jatrophane 1 or jatrophane 6 derivative, m/z 597.

Jakupovic et al (1998a) have proposed that the paraliane class of compounds are intermediates in the pathway between jatrophanes and pepluane. Since anti-cancer cell activity and dendritic cell reversal by both jatrophanes and pepluane have been demonstrated in this invention, it seems reasonable to conclude that the paralianes will also exhibit these properties.

EXAMPLE 11

Preparation of Material for the Mouse Experiments by Preparative Thin Layer Chromatography 15 ml crude sap in 70% ethanol was extracted with diethyl ether as described in Example 6. The extract was concentrated by vacuum centrifugation and resuspended in approx 5 ml DME. The DME extract was chromatographed on preparative TLC plates (Merck PLC, Silica gel 60, Cat no. 005745.1000) using hexane:ethyl acetate (4:1) as the developing solvent. Zones corresponding to regions "H" and "A–F" as shown in FIG. 12 were excised and combined, eluted with ether/DME, and dried by vacuum centrifugation. The extract was enriched in jatrophanes 2, 3 and 4, pepluane, and the ingenane acetate. The pellet was suspended in 95% ethanol and centrifuged at 10,000 g for 10 minutes. The supernatant (6.0 ml, 10 mg/ml) was distributed into 0.2 ml aliquots and stored at –20° C. This extract was assayed against MM96L melanoma cell line, and showed high potency, with dendritic cell morphology still evident at 1 in $5\times10^6$ dilution; this replicated the potency of the crude sap. The extract so prepared was enriched in jatrophanes 2, 3 and 4, pepluane, and the ingenane acetate. Just prior to injection, 20 μl was diluted to 1 ml with RPMI 1640 tissue culture medium containing 5% foetal calf serum for injection of 0.1–0.2 ml. The ethanol solution (10 mg/ml) was absorbed on a cotton bud (0.2–0.4 ml) and used for topical application in mice.

EXAMPLE 12

Inhibition of Growth of Subcutaneous Implants of Tumour Cells (a) Five 4 week old nude mice were injected s.c. at 4 different sites with 0.1 ml of tissue culture medium containing $2\times10^6$ MM96L human melanoma cells. The three treated mice were injected on days 1, 2, 3, 5, 6, 7, and 8 with 0.1 ml RPMI medium containing 5% foetal calf serum and 20 μg ethanol extract. In addition, the treated mice received up to four topical applications of approx 5–10 μl of 10 mg/ml ethanol extract or crude undiluted sap. Two separate sites on each treated mouse received topical treatment with either ethanol extract or crude sap. One mouse received topical treatment on days 12, 13 and 14, and the other two treated mice received topical treatment on days 15, 19, 20 and 22. Tumour volume was measured on day 32.

Prior to the topical applications, injection of extract had no apparent effect on tumour volume. Following topical application of ethanol extract there was an overnight change in tumour appearance. The tumours became greyish-black in colour, then developed a hard, lumpy black appearance followed by scab formation. Tumours treated with crude sap showed similar changes a day later. With time, the overall effects of ethanol extract and crude sap were similar, so measurements for the topically treated lesions have been combined. On the mice given injection plus topical treatment, tumour volume was reduced by 76% (p<0.2). One tumour which had been treated with the ethanol extract had completely disappeared, as shown in FIG. 13, and eight others were reduced to flat black scabs. The other three treated tumours initially showed similar colour changes and tumour regression, but had regrown following cessation of topical treatment 10 days before the measurements were taken.

(b) Six 4 week old C57 Black (C57B1) mice were injected with 0.1 ml of tissue culture medium containing $10^5$ B16 melanoma cancer cells at two sites on the underbelly. The tumours were allowed to develop for 4 days, and then were subjected to a regimen of three injections (20 μg ethanol extract in 0.1 ml RPMI medium containing 5% foetal calf serum (days 1, 2 and 4) and 1 topical treatment (5–10 μl of 10 mg/ml ethanol extract on day 4). 8 days after the first injection the areas of the tumours were measured using a ruler. Treatment reduced the size of the B16 melanoma tumours by 64% (p<0.05) on the three treated mice by comparison with the size of tumours on the three control mice.

The results are summarised in Table 18.

TABLE 18

Inhibition of Tumour Growth In Vivo by *E. peplus* Extracts

| Model | Treatment regimen | No of tumours | Tumour size* control | Tumour size* treated | % inhibition |
|---|---|---|---|---|---|
| MM96L human melanoma cell line, on nude mice | (a) | 12 | 89.8 ± 37 | 21.5 ± 3.6 | 76 (p < 0.20) |
| B16 mouse melanoma on C57B1 Black mice | (b) | 6 | 58.5 ± 9.5 | 21.2 ± 10.6 | 64 (p < 0.05) |

*(a) volume, $mm^3$,
(b) area, $mm^2$,.

EXAMPLE 13

Changes in Gene Expression Induced in a Human Melanoma Cell Line (MM96L) by Purified Extract Human melanoma cells of the MM96L cell line, cultured in 150 $cm^2$ plates in RPMI 1640 medium containing 10% foetal calf serum, were incubated with purified extract for 4 hr at 37° C. in 5% $CO_2$/air. Cells were washed with phosphate buffered saline (PBS), scraped in PBS, pelleted, resuspended in 1 ml PBS, pelleted and taken up in 300 μl NP-40 lysis buffer, left on ice for 15 min, pelleted and the supernatant treated with proteinase K and SDS at 37° C. for 15 min, extracted with phenol chloroform and the total RNA precipitated by ammonium acetate/ethanol at −20° C. overnight. The Promega mRNA isolation kit was used to isolate mRNA, which was then reverse transcribed in the presence of $^{33}$P-labelled dCTP to generate cDNA. The latter was hybridised on a Genome Systems human Gene Discovery Array 1.2 (GDA) according to the manufacturer's instructions. The array was quantitated with a Molecular Dynamics PhosphorImager, and analysed with ImageQant and Excel software.

The ratio of duplicate spot volumes from treated and untreated cells was calculated, and used to define the level of gene activation (ratio>1) or inhibition (<1). Backgrounds were typically 500–1000 counts, but were not subtracted; thus the stated ratios will tend to be underestimates of the actual changes.

The array contained cDNA spots from over 18,000 unique sequences, so-called expressed sequence tags (ESTs), of which approximately 3000 were from identifiable expressed genes of human cells. Many EST sequences in the human melanoma cells tested were either up- or down-regulated by the extract treatment. Only changes based on duplicates which had standard deviations <30% of the ratio were considered to be biologically significant at this stage. It should also be noted that a relatively short treatment time of 4 hr was used in order to identify the earliest and most critical targets for the agent. It is likely that further, major changes in gene expression, dependent upon the primary response, will occur after this time.

Results from the changes in level of the transcripts of some relevant known genes, considered to be beneficial either directly or indirectly for the control of cancer cells, are summarized in Table 19.

The changes in cell morphology observed in the Examples can be expected to result from the major down-regulation of a number of proteins that bind to actin, a major cytoskeletal protein. An increase in the retinol binding protein may also be involved here, as well as in induction of the differentiated phenotype through increasing the intracellular level of retinoids.

Repair of current and future DNA damage induced by solar UV irradiation may be enhanced by the observed induction of XP repair proteins. In addition, the decrease in GADD45 and ionising radiation resistance protein (DAP3) may be useful in sensitising tumour tissue to radiotherapy. The latter change is also notable because it is strongly upregulated in MM96L cells by UVB, the cause of skin cancer and melanoma.

A number of molecules relevant to enhancing the immune response were induced, particularly G-CSF. Some of these, such as proteins of the major histocompatability complex (MHC), are considered to be useful attributes for immunotherapy, enhancing killer T-cell activity.

The changes most significant for control of cell growth relate to the detected alterations of the G-protein and PKC pathways, and enhancement of proteosome activity. Intracellular signalling is critical for many cell processes, including proliferation and alterations in the normal equilibrium of pathways and pathway interactions, such as those mediated by Ras signalling, are likely to have adverse consequences for the cell. The level of induction of the proteosome component LAMP7-E1 was among the highest found for any gene in the experiment, and would be expected to greatly alter the processing of many proteins via the ubiquitin pathway.

On the basis of the gene expression array data, the compounds of this invention are expected to have activity:

1. In modulating gene expression in the G-protein, PKC and Ras signalling pathways, in a manner that leads to anticancer activity in vivo.

2. In ameliorating damage from solar UV and like agents, by enhancing DNA repair and the immune response, either in the target or effector cells.

3. As an adjuvant to radiotherapy or to therapy with other DNA-damaging agents, on the basis of down-regulation of protective proteins (GADD45 and DAP3).

TABLE 19

| Function | Gene | EGAD no. | Regulation by Extract | Reference |
|---|---|---|---|---|
| Immune response | Sialyltransferase MHC class 1 proteins | HT4978 | 2.16 | Li et al, 1998 |
|  | G-CSF receptor | HT3059 | 2.64 |  |
|  |  | HT2680 | 1.39 |  |
|  |  | HT4313 | 11.68 |  |
| Cell growth regulation | 80H-K | HT1772 | 2.11 | Kanai et al, 1997 |
|  | Fibroblast growth factor 9 | HT2447 | 0.59 |  |
| Differentiation | Cellular retinol binding protein 1 | HT2520 | 2.69 | Perozzi et al, 1998 |
| G-protein pathways | Beta polypeptide 3 | HT484 | 2.27 |  |
|  | G-binding protein | HT3752 | 0.35 |  |
|  | Small G protein TTF | HT5016 | 0.47 |  |
| PKC pathways | Phospholipase D | HT2473 | 4.04 | Bosch et al, 1998 |
|  | PKC zeta | HT21136 | 0.67 |  |
| Tumour suppressor genes | Wilm's tumour-related protein | HT3751 | 1.99 |  |
| DNA damage and repair proteins | XP group C p58 | HT4209 | 2.36 |  |
|  | Hsp 27/28 | HT2997 | 2.36 |  |
|  | XP group C HHR2 | HT4247 | 2.09 |  |
|  | GADD45 | HT3135 | 0.63 |  |
|  | Ionising radiation resistance protein (DAP3) | HT5168 | 0.46 |  |
| Proteolysis | LAMP7-E1 | HT3850 | 26.91 | Mimnaugh et al, 1997 |
| Cell morphology | Profilin II | HT928 | 0.62 | Djafar-zadeh, 1997 |
|  | Cofilin | HT1657 | 0.56 |  |
|  | Cyclophilin B | HT1953 | 0.36 |  |
|  | Tubulin alpha k1 | HT1813 | 0.61 |  |
| Oncogenes | TAX | HT3360 | 0.32 | Pise-Masison et al 1998 |

EXAMPLE 14

Treatment of a Solar Keratosis in a Human Volunteer

Ethics committee approval was obtained from the Queensland Institute of Medical Research for a clinician-supervised trial of use of crude sap of *E. peplus* for treatment of a facial solar keratosis in a human subject.

Crude extract obtained from Australian-grown plants and stored in 50% glycerol for 2 weeks at −20° C. was applied with a cotton bud applicator to the surface of a clinically diagnosed solar keratosis, approximately 5 mm in diameter, on the left temple of the face of a male human volunteer. Approximately 50 μl was delivered to the surface. One day later, a second application was made to the same site. After the first application, no reaction was noted for 4–5 h, whereafter an inflammation reaction occurred at the site and extended to an area of 80–100 mm in diameter. One day later, there was localised swelling, and blister formation at the site of application and on localised patches distal to the area of application, as if new premalignant sites were also targeted. After four days following the first treatment, the swelling subsided and scab formation was evident at the affected sites. After fourteen days, the scabs had sloughed off, leaving new skin underneath. After six weeks, the treated areas still had a pinkish tinge, but there was no sign of the original solar keratosis. As a control, a 1 cm$^2$ patch of normal skin on the forearm of the same volunteer was similarly treated. There was localised mild inflammation, which disappeared 7–10 days after treatment.

The strong inflammatory reaction associated with treatment of the solar keratosis could reflect recruitment and proliferation of killer-T cells, as suggested by the results for immune response obtained from the gene array screen in Example 13, and the observation of in vitro proliferation of T-cells by *E. peplus* crude sap in Example 15 below. Enhancement of killer-T cell activity is considered to be a key step in destruction of cancer cells by the immune system and may help to explain the recognition and attack of premalignant lesions distal to the site of original treatment.

EXAMPLE 15

Effect of Crude Sap and Purified Fractions "A" and "H" from TLC on Normal Melanocyte Cell Numbers 12-O-tetradecanoylphorbol-13-acetate (TPA) is essential for the culture of normal melanocytes in vitro, since these cells grow very poorly without TPA. In a preliminary experiment, *E. peplus* fractions were added to medium without added TPA from the start of the experiment. *E. peplus* fractions were added to fresh medium, and the cell numbers scored compared to fresh media without *E. peplus* fractions or TPA. Under this regimen, higher numbers of melanocytes were obtained than with the "control" cells grown in TPA-deficient medium. Interestingly, the cells in the medium with *E. peplus* fractions looked healthier than those cells grown in so-called "standard" medium with TPA. Thus *E. peplus*-derived compounds may provide a superior alternative to the use of TPA as a tool in cell culture.

In a second experiment, normal melanocytes were plated at 5000 cells per well, in RPMI 1640 medium containing 10% foetal calf serum, cholera toxin, antibiotics, and TPA. After 24 hours, the medium was removed from the cells by suction, and replaced with fresh medium without added TPA, but with the additions as specified. Cells were scored after a further 10 days of incubation. The results are shown in Table 20. It is evident that even at a 1 in 5,000,000 dilution a cell proliferation effect was noted with crude and purified fractions, in contrast to cell inhibitory effects observed at these concentrations against cancer cell lines as shown in earlier examples. In a separate test, in vitro proliferation of T cells was also obtained following treatment of T cells with crude *E. peplus* sap.

TABLE 20

| Sample | 1/50 | 1/500 | 1/5,000 | 1/50,000 | 1/500,000 | 1/5,000,000 |
|---|---|---|---|---|---|---|
| Solvent (control) | + | + | + | + | + | + |
| crude *E. peplus* sap | − | + | + | ++ | ++ | ++ |
| Fraction "A", (enriched in ingenol acetate) | + | ++ | ++ | ++ | ++ | + |
| Fraction "H", (enriched in jatrophane 3) | ± | ++ | ++ | ++ | ++ | ++ |

Scale:
+ = normal growth,
++ = approx 50% higher than normal growth

Since both normal melanocytes and T-cells were induced to proliferate by fractions from *E. peplus* sap, this agent may have wide application as a cell proliferation agent for normal cells, either in vivo or in vitro, in any medical condition where regeneration of normal cells would be advantageous, including but not limited to a) multiplication of skin cells (keratinocytes) for rapid wound healing in trauma cases and after surgery, and in recovery from burns.

b) multiplication of pancreatic islet cells for implantation
c) multiplication of T-cells and other cells of the immune system. It is interesting to note that the expansion of action past the point of application in the human volunteer trial on treatment of solar keratosis may be explained by a recruitment of natural killer-T cells to the region of application.
d) regeneration of aged or necrotic tissue from liver, kidney, colon, lung and eye.
e) multiplication of host tissue as an alternative to organ transplantation.

EXAMPLE 16

Effect of Betaines on Malignant Melanoma MM96L Cell Numbers

Betaines of different types were solubilised in sterile MilliQ™ water to a final concentration of 1 mg/ml, and diluted into 0.1 ml tissue culture medium containing 5000 MM96L cells as described previously. Cells were scored after 4 days incubation. The results are shown in Table 21.

Whereas most betaines tested had no effect on cell numbers, β-alanine betaine hydrochloride (homobetaine) depressed cell numbers at a final concentration of 20 μg/ml, and the cells had a dendritic appearance. t-4 hydroxy N,N-dimethyl proline also inhibited cell numbers at a final concentration of 20 μg/ml; however, the cell morphology changed to that of polydendritic forms, the significance of which is unknown.

It is envisaged that β-alanine betaine hydrochloride (homobetaine) may be a suitable formulation agent for $E.$ $peplus$ crude sap or its purified active principles, including ingenol, pepluane, and jatrophanes 1–6, either separately or in combination. This could be used for topical application against premalignant skin lesions at low dilutions of $E.$ $peplus$ principle(s), or formulated as an anticancer drug with higher concentrations of $E.$ $peplus$ principle(s). It has been suggested that betaines per se are useful as anti-cancer agents; see for example U.S. Pat. No. 5,545,667 by Wiersema et al.

Because of their surfactant properties, betaines are widely used as formulation ingredients in cosmetics. Due to their zwitterion properties, betaines could also assist transport of other ingredients into the deeper layers of the skin. A betaine to be used in a skin cosmetic preparation along with very dilute extracts of $E.$ $peplus$ sap or purified fractions derived therefrom, such as jatrophanes, pepluane, paraliane, or ingenane, separately or in combination, should desirably have complementary properties. Of all the betaines tested, including glycine betaine, only β-alanine betaine hydrochloride (homobetaine) had a phenotype reversal effect, albeit modest, as compared to $E.$ $peplus$ sap and fractions.

TABLE 21

| Sample | 1/50 | 1/500 | 1/5,000 |
| --- | --- | --- | --- |
| glycine betaine | +++ | +++ | +++ |
| N-methyl proline, free base | +++ | +++ | +++ |
| t-4-hydroxy N-methyl proline, free base | +++ | +++ | +++ |
| stachydrine (proline betaine), free base | +++ | +++ | +++ |
| t-3-hydroxy N-methyl proline, free base | +++ | +++ | +++ |
| β-alanine betaine hydrochloride (homobetaine) | ++d | +++ | +++ |
| t-4 hydroxy N,N-dimethyl proline, free base | +pd | +++ | +++ | d = dendritic morphology
pd = polydendritic morphology
Scale: +++ = no effect, − = complete cell death It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Beljanski M and Crochet, S. Int. J. Oncol., 1996 8 1143–1148
Belkin, M. and Fitzgerald, D. B. J. Natl. Cancer Inst., 1952 13 139
Bosch, R. R., Patel, A. M., Van Emst-de Vries, S. E., Smeets, R. L., De Pont, J. J., Willems, P. H., Pont, J. J. Eur J Pharmacol 1998 346 345–351
Djafarzadeh, S. Exp Cell Res. 1997 Nov. 1; 236(2) 1997, 236 427–435
Eke, T. Eye, 1994 8 694–696
Evans, F. J. and Kinghorn, A. D. Botanical Journal of the Linnean Society, 1977 74 23–35
Evans, I. A. and Osman, M. A. Nature, 1974 250 348
Falsone G et al, Farmaco., 1994 49 167–174
Fatope, M. O. et al J. Med. Chem., 1996 39 1005–1008
Francis, D. B., Hart, L. V., Wilson, P. R. and Beardmore, G. L. Med J. Aust., 1989 6 541–542
Galvez, J. et al Planta Med., 1993 59 333–336
Gundidza, M. et al Cent. Afr. J. Med., 1992 38 444–447
Guo, Z. et al Chung Kuo Chung Yao Tsa Chih, 1995 20 744–745
Hartwell, J. L. Lloydia 1969 32 153
Hecker, "Cocarcinogens from Euphorbiaceae and Thymeleaceae" in "Symposium on Pharmacognosy and Phytochemistry", 147–165 (Wagner et al, eds., Springer Verlag 1970).
Imai, S. Anticancer Research, 1954 14 933–936
Jakupovic, J., Morgenstern, T., Bitner, M. and Silva, M. Phytochemistry, 1998a 47 1601–1609
Jakupovic, J., Jeske, F., Morgenstern, T., Tsichritzis, F., Marco, J. A. and Berendsohn, W. Phytochemistry, 1998b 47 1583–1600
Jakupovic, J., Morgenstern, T., Marco, J. A. and Berendsohn, W. Phytochemistry, 1998c 47 1611–1619
Jurberg, P. et al Mem. Inst. Oswaldo Cruz, 1995 90 191–194
Kanai, M., Goke, M., Tsunekawa, S. and Podolsky, D. K. J Biol Chem 1997 272 6621–6628
Leung, A. Y. and Foster, A. Encyclopedia of Common Natural Ingredients Used Food, Drugs and Cosmetics, John Wiley & Sons, Inc. $2^{nd}$ edition, 1996
Li, M., Vemulapalli, R., Ullah, A., Izu, L., Duffey, M. E. and Lance, P. Am. J. Physiol., 1998 274 G599–G606
Liu. Y et al Chung Kuo Chung His Chieh Ho Tsa Chih, 1994 14 282–284
Marco, J. A., Sanz-Cervera, J. F., Yuste, A., Jakupovic, J. and Jeske, F. Phytochemistry, 1998 47 1621–1630
Matsumoto, T. et al Planta Med., 1992 58 255–258

Maynard, K. and Parsons, P. G. Cancer Res, 1986 46 5009–5013 Mimnaugh, E. G. Chen, H. Y., Davie, J. R., Celis, J. E. and Neckers, L. Biochemistry 1997 36 14418–14429

Moulin, A. et al Proc. Natl. Acad. Sci. USA, 1994 91 11328–11332

Oksuz, S. et al Phytochemistry, 1996 42 473–478

Pearn, J. Med. J. Aust., 1987 147 568–572

Perozzi. G, Barila, D., Plateroti, M., Sambuy, Y., Nobili, F. and Gaetani, S. Z. Ernahrungswiss, 1998 37 29–34

Pise-Masison, C. A., Radonovich, M., Sakaguchi, K., Appella, E. and Brady, J. N. J. Virol., 1998 72 6348–6355

Stavric, B. and Stoltz, D. R. Food Cosmet. Toxicol., 1976 14 141

Stirpe, F. et al Biochim. Biophys. Acta, 1993 1158 33–39

Sussman, L. A. E. and Liggins, D. F. Australian and New Zealand Journal of Surgery, 1996 66 276–278

Vijaya, K. et al J. Ethnopharmacol, 1995 49 115–118

Weedon, D. and Chick, J. Med. J. Aust., 1976 928 1–24

Yoshida, T. et al Chem. Pharm. Bull. (Tokyo), 1994 42 1803–1807

What is claimed is:

1. A method of treating a subject with cancer, the method comprising administering to the subject in need thereof a therapeutically effective amount of at least one isolated compound selected from the group consisting of an angeloyl-substituted ingenane obtained from the sap of a Euphorbia species and an active derivative of an angeloyl-substituted ingenane obtainable from the sap of a Euphorbia species, wherein said active derivative exhibits the same anti-cancer activity as said angeloyl-substituted ingenane.

2. The method of claim 1, wherein the Euphorbia species is *Euphorbia peplus*.

3. The method of claim 1, wherein the Euphorbia species is *Euphorbia drummondii*.

4. The method of claim 1, wherein the Euphorbia species is *Euphorbia hirta*.

5. The method of claim 2, wherein the derivative of an angeloyl-substituted ingenane obtained from the sap of *Euphorbia peplus* is an acetylated derivative.

6. The method of claim 3, wherein the derivative of an angeloyl-substituted ingenane obtained from the sap of *Euphorbia drummondii* is an acetylated derivative.

7. The method of claim 4, wherein the derivative of an angeloyl-substituted ingenane obtained from the sap of *Euphorbia hirta* is an acetylated derivative.

8. The method of any one of claims 1 to 4, wherein the at least one compound is selected from the group consisting of a 20-O-acetyl-ingenol-3-angelate and an ester derivative of a 20-O-acetyl-ingenol-3-angelate.

9. The method of any one of claims 1 to 4, wherein the compound comprises a pharmaceutically acceptable salt of the 20-O-acetyl-ingenol-3-angelate and the 20-O-acetyl-ingenol-3-angelate ester derivative.

10. The method of any one of claims 1 to 4, wherein the compound is obtained by the process of extracting said sap with 95% v/v ethanol, discarding a solid fraction and retaining a soluble fraction.

11. The method of any one of claims 1 to 4, wherein the cancer is a solid tumor.

12. The method of any one of claims 1 to 4, wherein the cancer is colon cancer.

13. The method of any one of claims 1 to 4, wherein the cancer is lung cancer.

14. The method of any one of claims 1 to 4, wherein the cancer is prostate cancer.

15. The method of any one of claims 1 to 4, wherein the cancer is cervical cancer.

16. The method of any one of claims 1 to 4, wherein the cancer is breast cancer.

* * * * *